(12) United States Patent
Kaula et al.

(10) Patent No.: US 9,931,511 B2
(45) Date of Patent: Apr. 3, 2018

(54) METHOD AND APPARATUS FOR VISUALIZING A MIGRATION HISTORY OF PAIN MAPS AND STIMULATION MAPS

(71) Applicant: Nuvectra Corporation, Plano, TX (US)

(72) Inventors: Norbert Kaula, Arvada, CO (US); Yohannes Iyassu, Denver, CO (US)

(73) Assignee: NUVECTRA CORPORATION, Plano, TX (US)

( * ) Notice: Subject to any disclaimer, the term of this patent is extended or adjusted under 35 U.S.C. 154(b) by 372 days.

(21) Appl. No.: 14/279,881

(22) Filed: May 16, 2014

(65) Prior Publication Data

US 2014/0344733 A1 Nov. 20, 2014

Related U.S. Application Data

(60) Provisional application No. 61/824,296, filed on May 16, 2013.

(51) Int. Cl.
| | |
|---|---|
| *G06F 3/0484* | (2013.01) |
| *A61N 1/372* | (2006.01) |
| *A61N 1/36* | (2006.01) |
| *G06F 3/0485* | (2013.01) |
| *G06F 19/00* | (2018.01) |
| *G06F 3/0482* | (2013.01) |

(52) U.S. Cl.
CPC ..... *A61N 1/37247* (2013.01); *A61N 1/36185* (2013.01); *G06F 3/0484* (2013.01); *G06F 3/0485* (2013.01); *G06F 3/04842* (2013.01); *G06F 3/04847* (2013.01); *G06F 19/3406* (2013.01); *G06F 19/3437* (2013.01); *G06F 3/0482* (2013.01); *G06F 19/3481* (2013.01)

(58) Field of Classification Search
CPC ..................................................... G06F 3/0484
USPC .......................................................... 715/765
See application file for complete search history.

(56) References Cited

U.S. PATENT DOCUMENTS

| | | | | |
|---|---|---|---|---|
| 5,938,690 A | * | 8/1999 | Law .................. | A61N 1/37235 607/46 |
| 5,966,126 A | * | 10/1999 | Szabo ................. | G06F 9/4443 707/E17.082 |

(Continued)

OTHER PUBLICATIONS

James Standen, "Inner and outer joins SQL examples and the Join block", posted on Feb. 10, 2010, avialable at <<http://www.datamartist.com/sql-inner-join-left-outer-join-full-outer-join-examples-with-syntax-for-sql-server>>, 3 pages.*

*Primary Examiner* — Reza Nabi
*Assistant Examiner* — Daniel Rodriguez
(74) *Attorney, Agent, or Firm* — Haynes and Boone, LLP; Eric Q. Li

(57) ABSTRACT

A method of visualizing a sensation experienced by a patient is disclosed. A graphical user interface is provided. The graphical user interface is configured to receive an input from a user and display a visual output to the user. A virtual control mechanism is displayed on the graphical user interface. One or more engagements of the virtual control mechanism are detected through the graphical user interface. In response to the engagement of the virtual control mechanism, a sensation map history is displayed on the graphical user interface. The sensation map history graphically depicts a migration of a sensation map over time on a virtual human body model.

27 Claims, 30 Drawing Sheets

(56) References Cited

U.S. PATENT DOCUMENTS

| | | | | |
|---|---|---|---|---|
| 6,611,846 B1* | 8/2003 | Stoodley | G06F 19/322 | 705/3 |
| 6,622,048 B1* | 9/2003 | Mann | A61N 1/36071 | 607/46 |
| 7,630,849 B2* | 12/2009 | DeSimas | G01N 31/00 | 600/1 |
| 2004/0049730 A1* | 3/2004 | Ishizaka | G06F 17/246 | 715/213 |
| 2004/0143302 A1* | 7/2004 | Sieracki | A61N 1/08 | 607/48 |
| 2006/0280287 A1* | 12/2006 | Esham | A61N 5/1049 | 378/65 |
| 2008/0154340 A1* | 6/2008 | Goetz | A61N 1/36185 | 607/59 |
| 2008/0160492 A1* | 7/2008 | Campbell | G09B 19/00 | 434/379 |
| 2009/0046898 A1* | 2/2009 | Li | G06F 17/30554 | 382/113 |
| 2010/0010566 A1* | 1/2010 | Thacker | A61N 1/36071 | 607/46 |
| 2010/0168820 A1* | 7/2010 | Maniak | A61N 1/36007 | 607/63 |
| 2010/0185181 A1* | 7/2010 | Alme | A61M 5/14276 | 604/891.1 |
| 2011/0172564 A1* | 7/2011 | Drew | A61B 5/061 | 600/587 |
| 2011/0172744 A1* | 7/2011 | Davis | A61M 5/14276 | 607/62 |
| 2011/0196654 A1* | 8/2011 | Genest | A61C 13/0004 | 703/1 |
| 2011/0208012 A1* | 8/2011 | Gerber | A61M 5/1723 | 600/300 |
| 2011/0258548 A1* | 10/2011 | Abujbara | G06Q 10/00 | 715/730 |
| 2011/0264165 A1* | 10/2011 | Molnar | A61N 1/36185 | 607/45 |
| 2011/0270358 A1* | 11/2011 | Davis | A61N 1/36185 | 607/60 |
| 2013/0104066 A1* | 4/2013 | Soederstroem | G06F 3/04847 | 715/771 |
| 2013/0116748 A1* | 5/2013 | Bokil | A61N 1/0534 | 607/59 |
| 2013/0282078 A1* | 10/2013 | Wacnik | A61N 1/36071 | 607/59 |
| 2014/0005744 A1* | 1/2014 | Hershey | A61N 1/37211 | 607/46 |
| 2014/0140591 A1* | 5/2014 | Arazi | G06F 19/321 | 382/128 |
| 2014/0280553 A1* | 9/2014 | Hernandez | H04L 67/22 | 709/204 |
| 2016/0220179 A1* | 8/2016 | Rigoard | A61B 5/1072 | |
| 2017/0128722 A1* | 5/2017 | Perez | A61B 5/6833 | |

* cited by examiner

METHOD AND APPARATUS FOR VISUALIZING A MIGRATION HISTORY OF PAIN MAPS AND STIMULATION MAPS

PRIORITY DATA

The present application is a utility application of provisional U.S. Patent Application No. 61/824,296, filed on May 16, 2013, entitled "Features and Functionalities of an Advanced Clinician Programmer," the disclosure of which is hereby incorporated by reference in its entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implanted medical devices (for example a neurostimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient. Advances in the medical device field have improved these electronic programmers. For example, some existing programmers allow the creation and display of pain maps and stimulation maps as part of the pain diagnosis and communication with the patient. However, the pain maps and stimulation maps on existing programmers have certain shortcomings. For example, conventional systems and methods of displaying pain maps and/or stimulation maps typically display the pain maps and/or stimulation maps at a single snapshot in time. As another example, conventional systems and method may not offer the user a clear and intuitive representation of how a pain map is overlapped with a stimulation map or with another pain map. Therefore, conventional methods of displaying pain maps and stimulation maps may not give the healthcare professional sufficient information to effectively treat the patient.

Therefore, although existing systems and methods for generating and displaying pain maps and stimulation maps have been generally adequate for their intended purposes, they have not been entirely satisfactory in every aspect.

SUMMARY

One aspect of the present disclosure involves an electronic device for visualizing a sensation experienced by a patient. The electronic device includes: a graphical user interface configured to receive an input from a user and display a visual output to the user; a memory storage component configured to store programming code; and a computer processor configured to execute the programming code to perform the following tasks: displaying a virtual control mechanism on the graphical user interface; detecting, through the graphical user interface, one or more engagements of the virtual control mechanism; and displaying, in response to the engagement of the virtual control mechanism, a sensation map history on the graphical user interface, wherein the sensation map history graphically depicts a migration of a sensation map over time on a virtual human body model.

Another aspect of the present disclosure involves a medical system. The medical system includes: one or more medical devices configurable to deliver a medical therapy to a patient; and an electronic device configured to program the one or more medical devices. The electronic device includes: a graphical user interface configured to receive an input from a user and display a visual output to the user; a memory storage component configured to store computer instructions; and a processor component configured to execute the computer instructions to perform the following tasks: displaying a virtual control mechanism on the graphical user interface; detecting, through the graphical user interface, one or more engagements of the virtual control mechanism; and displaying, in response to the engagement of the virtual control mechanism, a sensation map history on the graphical user interface, wherein the sensation map history graphically depicts a migration of a sensation map over time on a virtual human body model.

Yet another aspect of the present disclosure involves method of visualizing a sensation experienced by a patient. The method includes: providing a graphical user interface configured to receive an input from a user and display a visual output to the user; displaying a virtual control mechanism on the graphical user interface; detecting, through the graphical user interface, one or more engagements of the virtual control mechanism; and displaying, in response to the engagement of the virtual control mechanism, a sensation map history on the graphical user interface, wherein the sensation map history graphically depicts a migration of a sensation map over time on a virtual human body model.

One more aspect of the present disclosure involves an electronic apparatus. The electronic apparatus includes: means for receiving an input from a user and displaying a visual output to the user; means for displaying a slider bar and a marker movable along the slide bar, wherein a length of the slider bar corresponds to a predefined period of time; means for detecting a movement of the marker along the slider bar; and means for displaying, in response to the detected movement of the marker along the slider bar, a sensation map history that graphically depicts, on a virtual human body model, a migration of pain or stimulation experienced by the patient over the predefined period of time, and wherein the means for displaying the sensation map history comprises means for automatically updating the displayed sensation map history in real time as the marker is moved along the slider bar.

Yet another aspect of the present disclosure involves an electronic device. The electronic device includes: a graphical user interface configured to receive an input from a user and display a visual output to the user; a memory storage component configured to store programming code; and a computer processor configured to execute the programming code to perform the following tasks: concurrently displaying a first map and a second map via the graphical user interface, wherein the first map and the second map are each a pain map or a stimulation map, wherein the pain map represents a body area of the patient experiencing pain, and wherein the stimulation map represents a body area of the patient experiencing electrical stimulation; displaying a virtual control mechanism via the graphical user interface; detecting, through the graphical user interface, an engagement of the virtual control mechanism; and adjusting, in response to the engagement of the virtual control mechanism, a respective visual emphasis of the first map and the second map, further comprising: increasing a visual emphasis of at least a portion of the first map while decreasing a visual emphasis of at least a portion of the second map; or decreasing the visual emphasis of at least a portion of the first map while increasing the visual emphasis of at least a portion of the second map.

Another aspect of the present disclosure involves a medical system. The medical system includes one or more medical devices configurable to deliver a medical therapy to a patient and an electronic device configured to program the one or more medical devices. The electronic device includes: a graphical user interface configured to receive an input from a user and display a visual output to the user; a memory storage component configured to store computer instructions; and a processor component configured to execute the computer instructions to perform the following tasks: concurrently displaying a first map and a second map via the graphical user interface, wherein the first map and the second map are each a pain map or a stimulation map, wherein the pain map represents a body area of the patient experiencing pain, and wherein the stimulation map represents a body area of the patient experiencing electrical stimulation; displaying a virtual control mechanism via the graphical user interface; detecting, through the graphical user interface, an engagement of the virtual control mechanism; and adjusting, in response to the engagement of the virtual control mechanism, a respective visual emphasis of the first map and the second map, further comprising: increasing a visual emphasis of at least a portion of the first map while decreasing a visual emphasis of at least a portion of the second map; or decreasing the visual emphasis of at least a portion of the first map while increasing the visual emphasis of at least a portion of the second map.

One more aspect of the present disclosure involves a method of displaying pain or stimulation experienced by a patient. The method includes: providing a graphical user interface configured to receive an input from a user and display a visual output to the user; concurrently displaying a first map and a second map via the graphical user interface, wherein the first map and the second map are each a pain map or a stimulation map, wherein the pain map represents a body area of the patient experiencing pain, and wherein the stimulation map represents a body area of the patient experiencing electrical stimulation; displaying a virtual control mechanism via the graphical user interface; detecting, through the graphical user interface, an engagement of the virtual control mechanism; and adjusting, in response to the engagement of the virtual control mechanism, a respective visual emphasis of the first map and the second map, further comprising: increasing a visual emphasis of at least a portion of the first map while decreasing a visual emphasis of at least a portion of the second map; or decreasing the visual emphasis of at least a portion of the first map while increasing the visual emphasis of at least a portion of the second map; wherein the providing of the graphical user interface, the concurrently displaying the pain map and the stimulation map, the displaying of the virtual control mechanism, the detecting of the engagement of the virtual control mechanism, and the adjusting of the respective visual emphasis are each performed by one or more electronic processors.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

Figure 1:
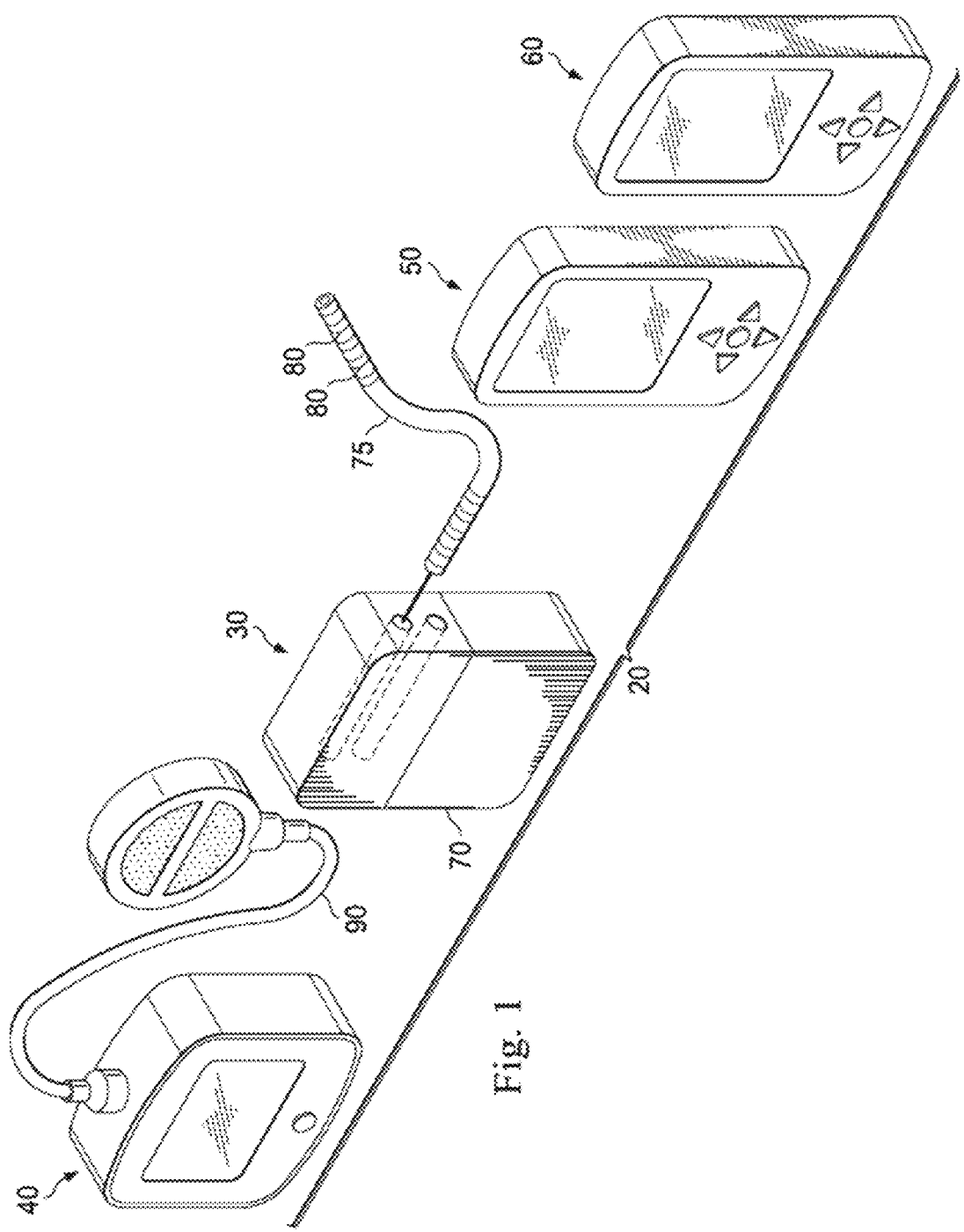
FIG. 1 is a simplified block diagram of an example medical environment in which evaluations of a patient may be conducted according to various embodiments of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn to different scales for simplicity and clarity.

In recent years, the use of active implanted medical devices has become increasingly prevalent. Some of these implanted medical devices include neurostimulator devices that are capable of providing pain relief by delivering electrical stimulation to a patient. In that regards, electronic programmers have been used to configure or program such neurostimulators (or other types of suitable active implanted medical devices) so that they can be operated in a certain manner. Such electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, such electronic programmers have achieved significant improvements, for example, improvements in size, power consumption, lifetime, and ease of use. For instance, electronic programmers have been used to generate and/or display pain maps and stimulation maps (which may be collectively referred to as sensation maps) for a patient. In general, a pain map shows the location or intensity of a patient's pain, and a stimulation map shows the location or intensity of the electrical stimulation (e.g., stimulation delivered by the neurostimulator) perceived by the patient. Such pain/stimulation maps can serve as useful tools for diagnosing the patient's pain and treatment and also allow visual/non-verbal communication between a patient and a healthcare professional. In addition, a history of the maps, if collected, can provide a record of a patient's treatment progress, and the maps can also be analyzed across patient groups. In some embodiments, to protect patient privacy, the personal information of the patients is stripped before the history of the pain/stimulation maps are collected and analyzed. In other words, the history of the pain/stimulation maps may be collected and analyzed anonymously in certain embodiments.

Nevertheless, the generation and display of pain/stimulation maps in existing programmers in the medical field may still have drawbacks. For example, conventional systems and methods are not capable of providing a migration history of a pain map and/or a stimulation map over a period of time. As another example, conventional systems and methods do not have the capability to compare different pain maps or different stimulation maps that are acquired at different points in time. As yet a further example, conventional systems and methods are not capable of producing an intuitive and user-interactive pain map and stimulation map overlap coverage. As such, a healthcare professional may not be able to effectively diagnose and treat the target patient.

To overcome these problems associated with existing electronic programmers discussed above, the present disclosure offers a programmer that allows for the generation and display of a migration history of pain maps and/or stimulation maps over time. The migration history may be displayed as a time-lapse video or animation sequence in some embodiments. The time-lapse video or animation sequence fully illustrates how the boundaries of the pain map and/or stimulation map move over time, along with the changing of the time or date information. In this manner, the healthcare professional can accurately determine how the pain or stimulation has evolved in the past and how they are likely to evolve in the future. Therefore, the healthcare professional can develop a better treatment plan for the patient. The various aspects of the generation and display of the migration history of the pain/stimulation maps are discussed in more detail below.

FIG. 1 is a simplified block diagram of one embodiment of a medical device system 20 to provide an example context for the various aspects of the present disclosure. The embodiment of the medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2, 3A-3B, 4A-4B, 5A-5B, and 6-15 are example screenshots of a user interface 100 for generating and displaying sensation maps (e.g., pain/stimulations maps) according to the various aspects of the present disclosure. In some embodiments, the user interface 100 may be displayed on a screen of a programmer. In some embodiments, the screen may be a capacitive or resistive touch-sensitive screen. In other embodiments, the screen may be a non-touch-sensitive screen, for example a Liquid-Crystal Display (LCD) screen, a Light-Emitting Diode (LED) screen, or a Cathode Ray Tube (CRT) screen. In yet other embodiments, the user interface 100 may be displayed on a programmer and an external monitor simultaneously, for example in accordance with U.S. patent application Ser. No. 13/600,875, filed on Aug. 31, 2012, entitled "Clinician Programming System and Method", the disclosure of which is hereby incorporated by reference in its entirety. As such, both the healthcare provider and the patient are able to view the user interface at the same time.

Figure 2:
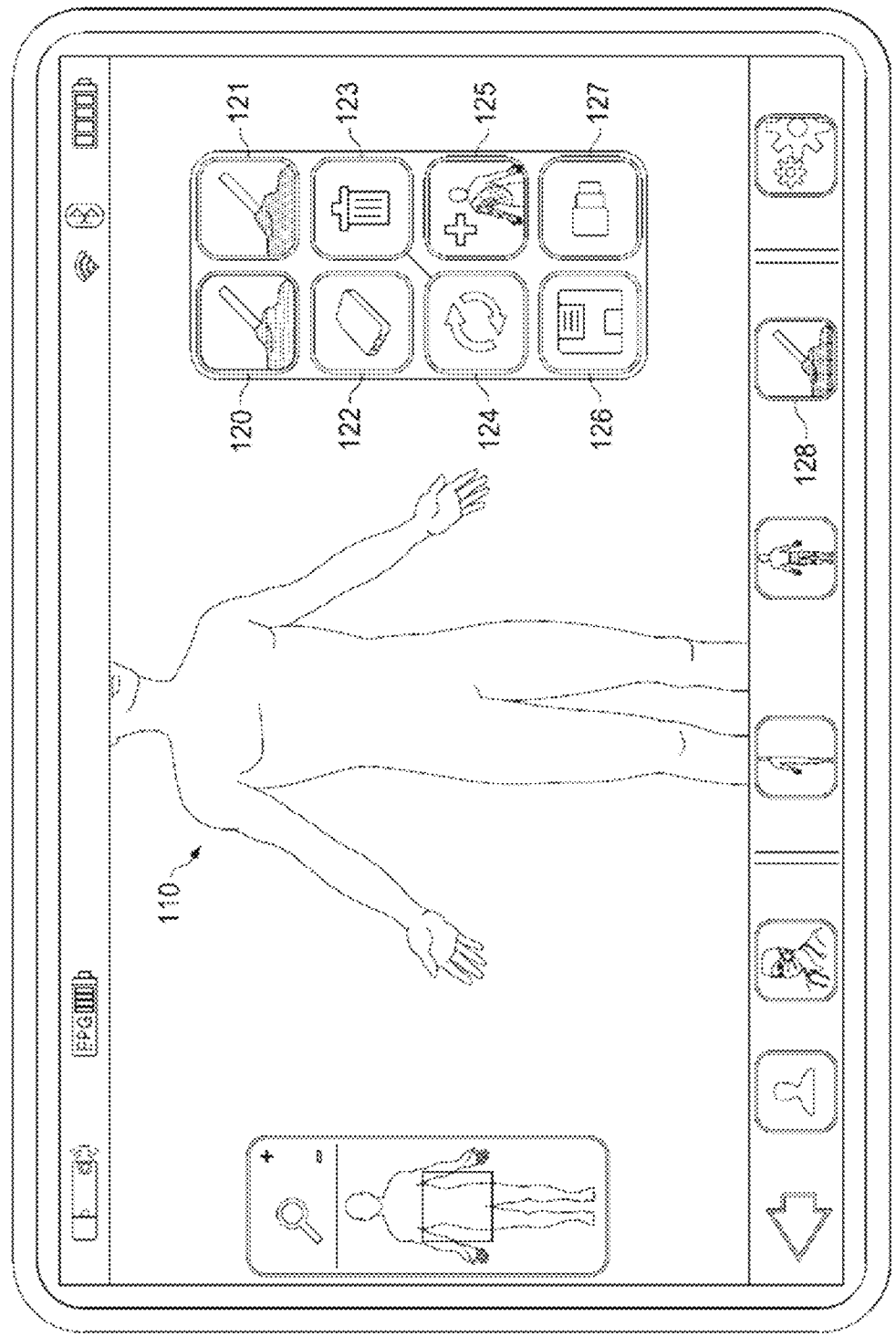
FIGS. 2, 3A-3B, 4A-4B, 5A-5B, and 6-25 are graphical user interfaces for generating and displaying pain/stimulation maps according to various aspects of the embodiments disclosure.

Referring to FIG. 2, the user interface 100A illustrates a 3D model of a human body 110. The 3D human body model 110 includes an entire human body, though the user interface 100 may be configured to view only a portion of the human body model 110 at a time. The human body model 110 can also be moved in all directions, rotated, resized, or otherwise manipulated. In some embodiments, the human body model 110 is customized for a specific patient. For instance, if a patient is tall (e.g., 6 feet or taller), the human body model 110 may be created (or later resized) to be "taller" too, so as to correspond with the patient's height. As another example, if the patient is overweight or underweight, the human body model 110 may be created (or later resized) to be wider or narrower, so as to correspond with the patient's weight. As other examples, if the patient has particularly long or short limbs (or even missing limbs or body parts), hands/feet, or a specific body build, the human body model 110 may be created (or later resized) to correspond with these body characteristics of the patient as well.

In some embodiments, the present disclosure offers a database that includes a plurality of predefined human body models that each correspond to a specific body type, for example a predefined body type for a 40 year old Caucasian male with a height of 6'1 and a weight of 200 pounds, or a 20 year old African American female with a height of 5'5 with a weight of 120 pounds, so on and so forth. In these embodiments, a healthcare professional or the patient can quickly select a predefined body type from this database that most closely matches his/her physical conditions/characteristics. In this manner, the healthcare professional need not spend too much time specifically customizing the human body model 110 to the patient, since a predefined human body model that is substantially similar to the patient is already available from the database. It is also understood that such database may be available to a network of healthcare professionals and may be downloaded to the electronic programmer upon verifying the necessary login credentials. The patient models may also be uploaded from an electronic programmer to the database. In some further embodiments, the clinician programmer discussed herein is configured to capture an image of the patient (for example via an integrated camera). The proportions and other bodily details of the patient may then be automatically adjusted by processing the captured patient image.

Figure 3A:
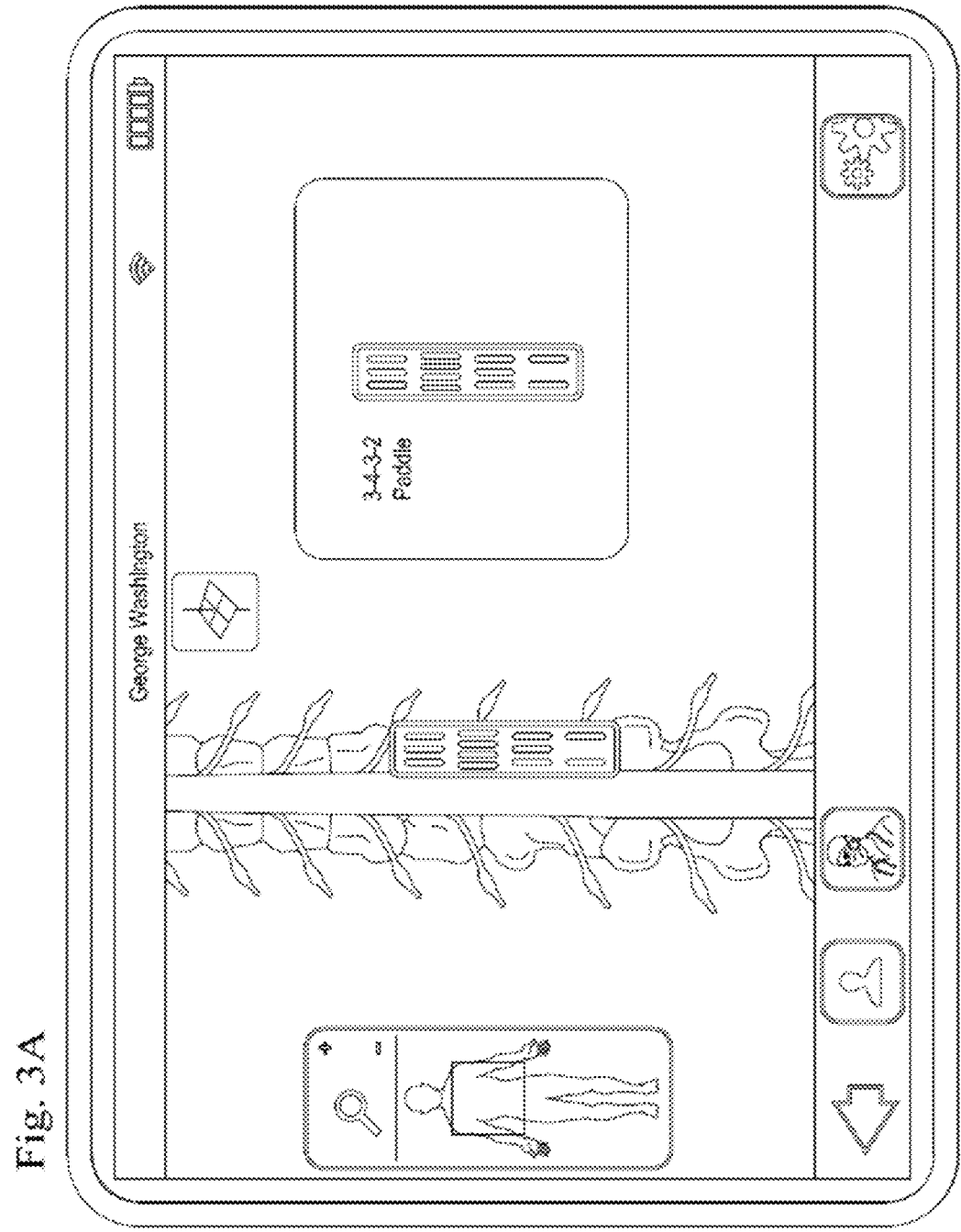
Figure 3B:
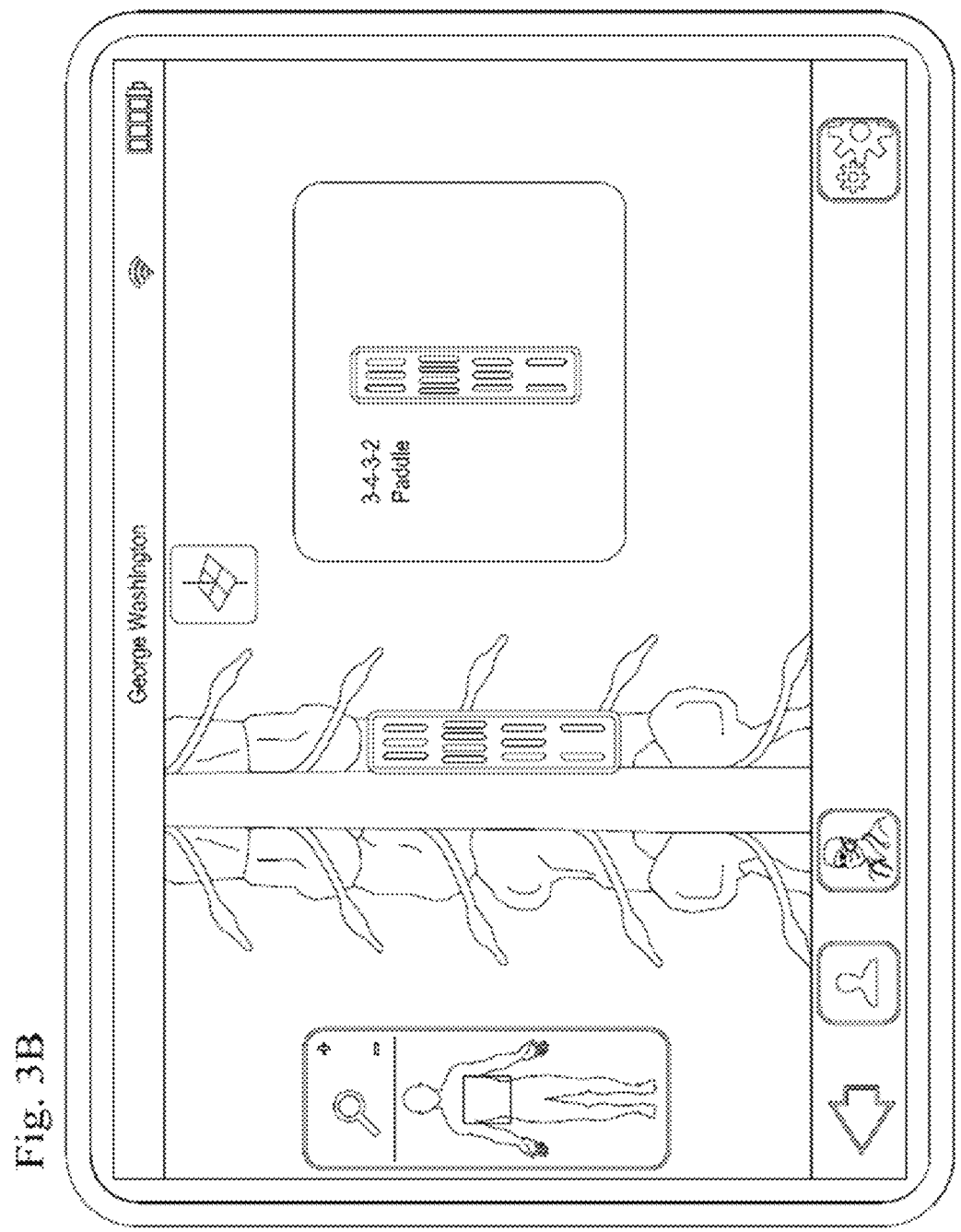

FIGS. 3A-5A, 3B-5B, and 6-9 are graphical examples illustrating how a human body model can be customized to more accurately match the physical traits of a patient. In more detail, FIGS. 3A-3B are graphical illustrations of an implanted medical device (e.g., a paddle lead) relative to a spine of a patient. In FIG. 3A, the patient is a short patient, and therefore the implanted medical device covers more vertebra levels. In comparison, the patient is a tall patient in FIG. 3B, and thus the implanted medical device covers fewer vertebra levels. This is because the spacing between the vertebra levels increase as the patient's height increases, but the length of the implanted medical device will remain the same regardless of the patient's height. Thus, FIGS. 3A-3B highlight the importance of matching the actual patient with a model as closely as possible, as the efficacy of the treatment is dependent on the accurate modeling.

Figure 4A:
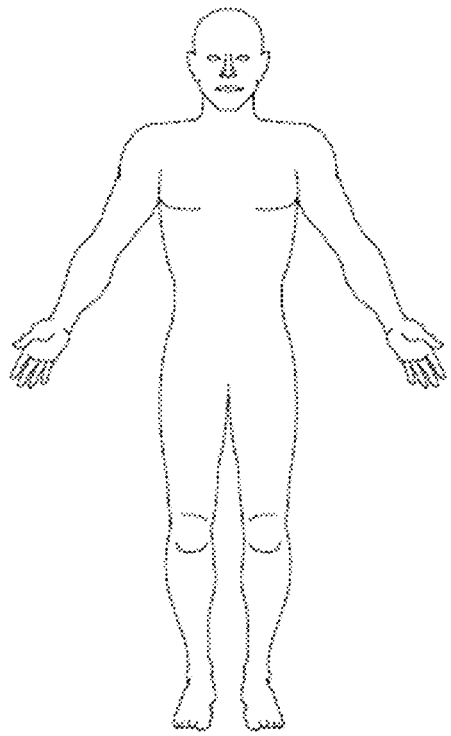
Figure 4B:
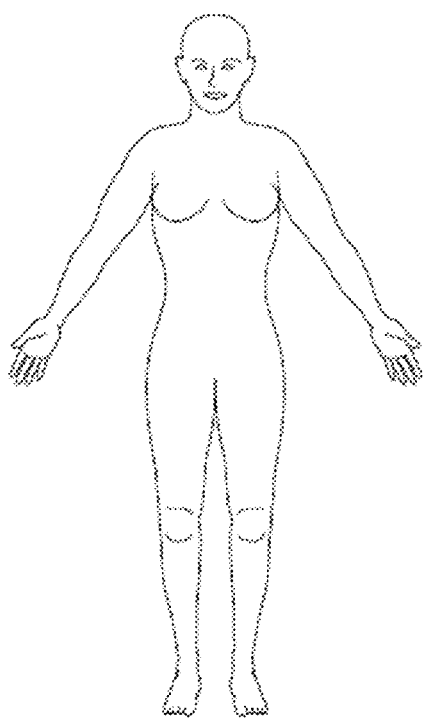
Figure 5A:
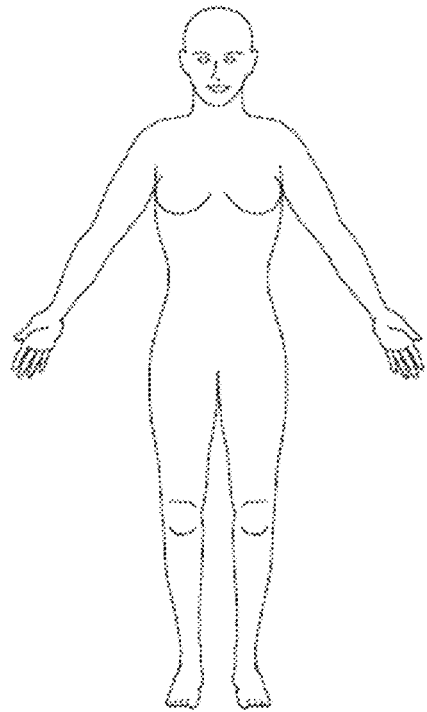
Figure 5B:
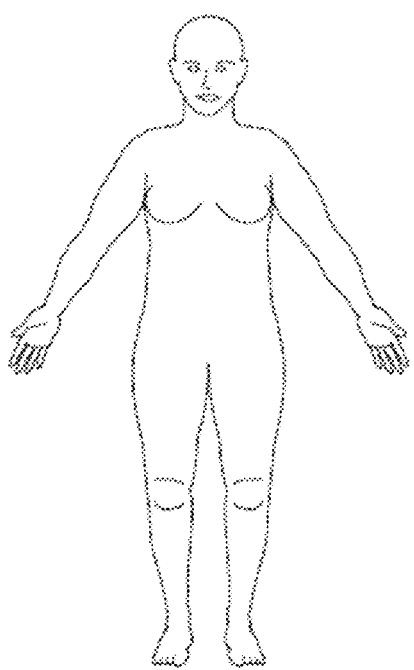
Figures 6, 7:
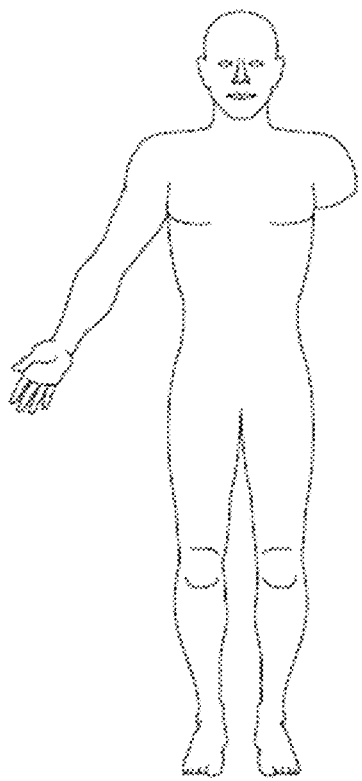

As discussed above, height is not the only variable that can be adjusted in customizing a human body model that closely matches the actual patient. Gender and weight are also among the variables that can be adjusted. As examples, FIG. 4A illustrates a standard male model, FIG. 4B illustrates a standard female model, FIG. 5A illustrates a tall and thin female model, and FIG. 5B illustrates a short and more heavy-set female model. Furthermore, another possible structural adjustment is the removal of appendages, which is illustrated in FIG. 6, where the model is missing a part of his left arm. The removal of appendages may be accomplished by not using all the vertices of the original model, for example. And although not specifically shown for reasons of simplicity, other variables that can be adjusted include skin color, hair color, eye color, etc.

FIG. 7 is an example patient information record in which the user (who may or may not be the patient) may enter patient specifics such as height, weight, gender, body type, etc. discussed above. In some embodiments, the patient record may be used to automatically modify the human body model representing the actual patient. In other embodiments, the user may manually adjust the human body model manually. In yet other embodiments, the user may make manual adjustments to the human body model after a human body model has been automatically generated based on the patient information entered into the patient record. For example, in FIG. 8, a standard male model has been generated for patient "John S. Doe" based on the data entered into his patient record. The user wants to make further manual adjustments to the automatically-generated model, and thus a list of modification options appears, which includes "Adjust Height," "Adjust Weight," "Adjust Skin Color," "Adjust Hair," and "Adjust Body Type." The user wishes to make an adjustment to the body type and selects the option "Adjust Body Type." As a result, a list of body type options appears, which includes "Ectomorph" (heavy/rounded), "Endomorph" (lean), and "mesomorph" (muscular).

Figure 8:
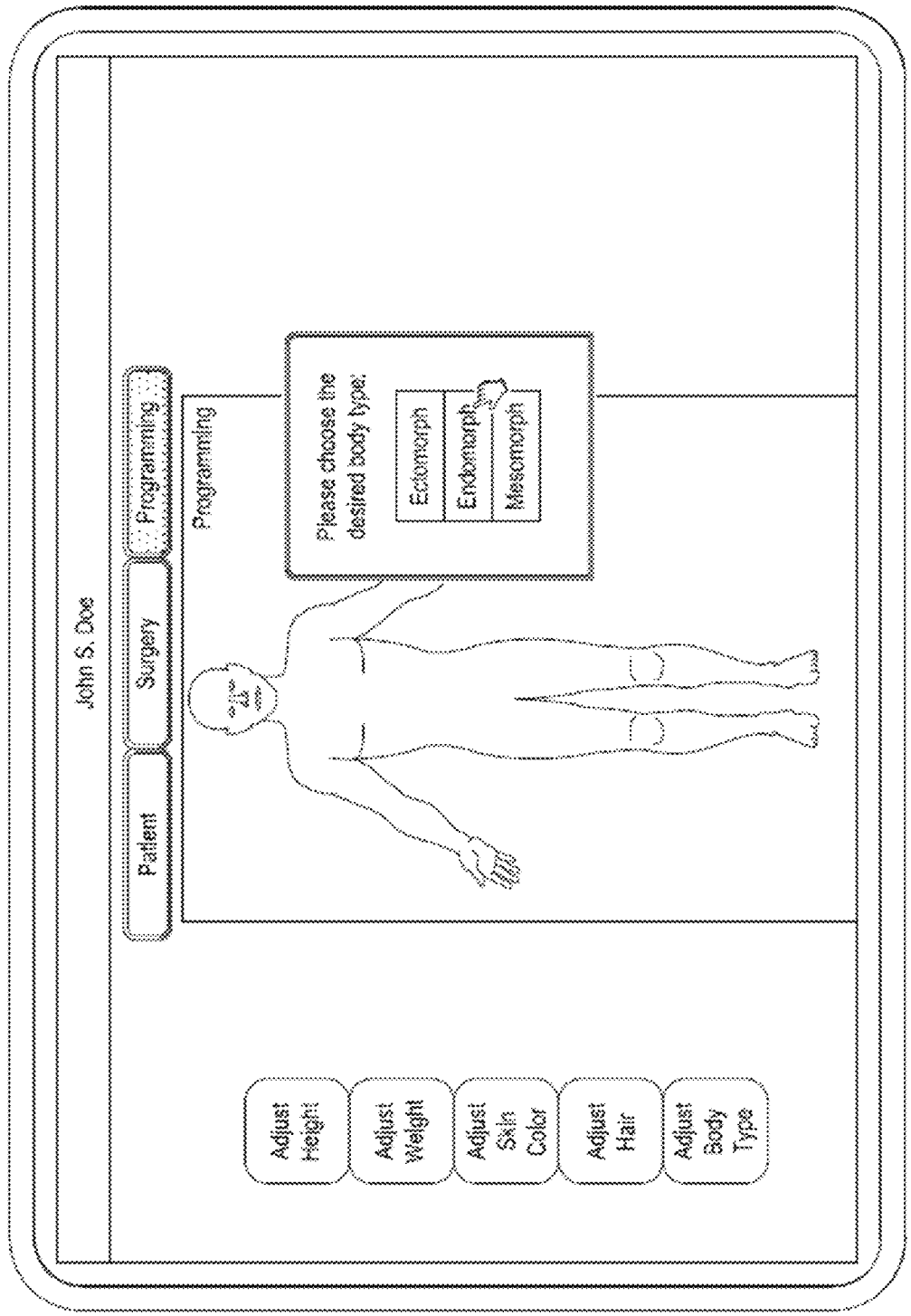
Figure 9:
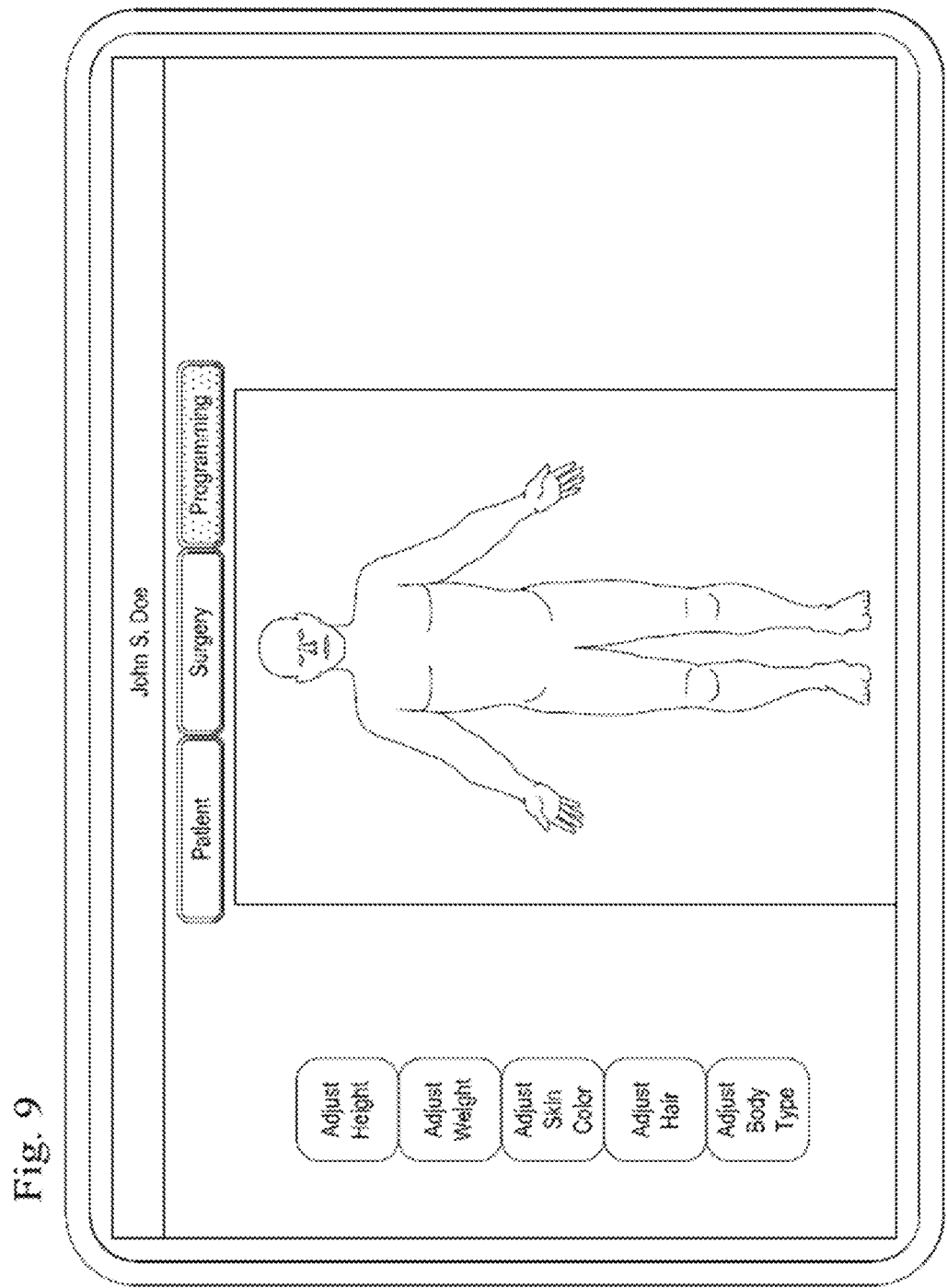

Referring now to FIG. 9, an adjusted model is shown as a result of the user selecting "Ectomorph." Thus, the model is FIG. 9 is heavier and more rounded compared to the model in FIG. 8 before the adjustment. Of course, these adjustment options discussed above are merely examples, and additional adjustment options are envisioned in other embodiments.

Referring now back to FIG. 2, the user interface 100 also displays a plurality of menu items 120-127 to assist with the generation and display of the pain maps and stimulation maps (not visible in FIG. 2). The display of the menu items 120-127 is triggered by the user pressing on a virtual button 128. In the illustrated embodiment, the menu item 120 is used to generate a pain map or a stimulation map. After selecting the menu item 120, the patient can user his/her finger(s) as a simulated brush to draw or paint an area on the human body model 110 that corresponds to a region of pain the patient experiences. For example, if the patient feels pain in his/her shoulder, he/she can paint a pain map on the shoulder region of the human body model 110. The human body model 110 can also be rotated, so that the patient can paint the pain map in different regions of the human body model. The patient may revise the pain map to correspond as closely with the actual perceived regions of pain as possible. To facilitate the painting/drawing of the pain maps, the simulated brush may be of adjustable size.

The stimulation map may be created in a similar manner, except that the stimulation map corresponds with the perceived stimulation (e.g., Paresthesia) experienced by the patient. The pain map and stimulation map are drawn on a touch-sensitive screen in the illustrated embodiment, but may be drawn via any other suitable type of user interface in other embodiments. A graphics accelerator may be used to speed up the generation of these maps.

Once the virtual button 128 is engaged to trigger the display of the menu items 120-127, the menu items 120-121 may be used to indicate different levels of intensity of the pain or stimulation. For example, referring to FIG. 10, after the menu item 120 is used to create a "baseline" pain map that covers a region of the body in general, the menu item 121 (shown in FIG. 2) may be used to indicate a region where the pain is more intense. In the embodiment shown in FIG. 10, the patient may draw a region 140 as a "baseline" pain region to indicate general pain. This region 140 may represent the body regions where the patient feels some degree of pain. The patient may also draw a region 142 within the region 142 as an "intense" or "acute" pain region. In other words, the patient may feel much more pain in the region 142 than in the rest of the region 140. The degree of the pain intensity may correspond with a color (or hue) of the region, and a variety of colors may be available to represent different degrees of pain.

Thus, a pain map of the present disclosure may reveal various regions with different degrees of pain. In some embodiments, the more painful regions are represented by darker colors, and the less painful regions are represented by lighter colors. The opposite may be true in other embodiments. In further embodiments, various pain maps may be created to represent different types of pain, for example a numbness, a burning pain, a tingling, a soreness, etc. These different types of pain may be represented by pain maps with different colors or different textures, for example. In yet other embodiments, the depth of pain (whether the pain is only skin-deep or penetrates to the muscle level) may also be represented by the pain maps, for example by different colors or different textures of the pain maps. It is also understood that the pain/stimulation maps may be resized proportionally to automatically correspond with the underlying human body model. That is, if the human body model on which the pain/stimulation maps are resized, the pain/stimulation maps may be resized accordingly.

Figure 10:
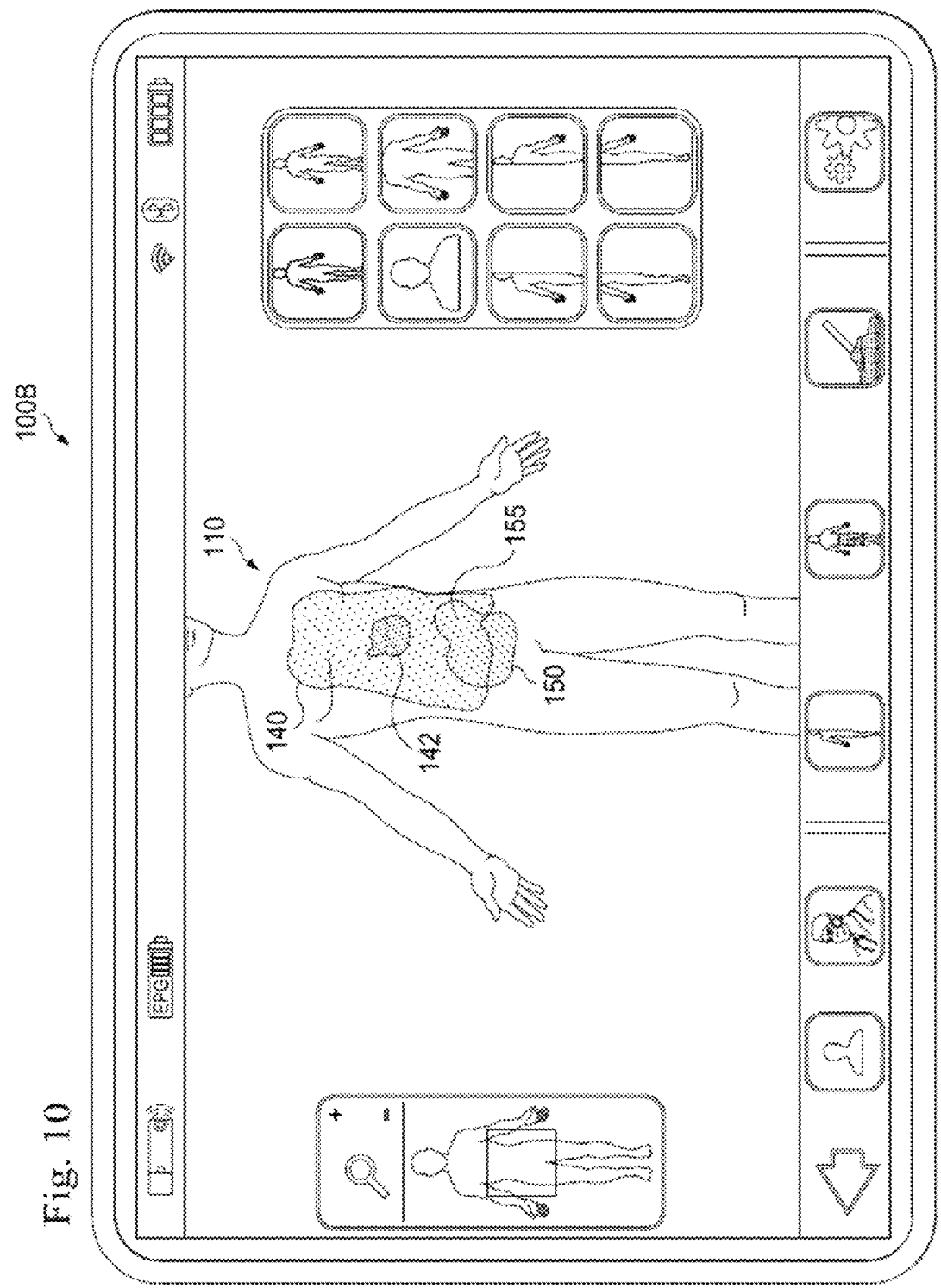

Similarly, the patient may also draw a region 150 to indicate a region on the body where the patient experiences stimulation while the stimulation therapy is active. The stimulation maps may be configured in a similar manner as the pain maps. In other words, the stimulation maps may be configured to portray different intensities of stimulation sensations, different regions of stimulation sensations, different types of stimulation sensations or different depths of stimulation sensations. Note that the pain region 140 and the stimulation region 150 may be displayed individually, or simultaneously, as shown in FIG. 10. An overlapping region 155 (an overlapping between the pain region 140 and the stimulation region 150) may also be displayed, which is helpful in helping the healthcare professional in diagnosing and treating the patient.

It is understood that although pain maps are used as an example herein for illustration purposes, stimulation maps containing regions with different stimulation intensity may be generated in the same manner.

Referring back to FIG. 2, the menu item 122 is used to erase or remove portions of the pain map or the stimulation map. This is done when the patient needs to revise an existing pain map or stimulation map, for example when the pain map or stimulation map is dated and no longer accurately reflects the patient's perceived pain or stimulation.

The menu item 123 is used to delete an existing pain map or stimulation map.

The menu item 124 is used to cycle through different maps, such as switching between pain maps and stimulation maps.

The menu item 125 is used to generate a new pain map or a new stimulation map (or updated versions of existing pain/stimulation maps).

The menu item 126 is used to save changes to a pain map or a stimulation map.

The menu item 127 is used to play back a migration of pain maps and stimulation maps, or a combination thereof. The migration of the pain maps and stimulation maps may be historical (i.e., in the past) or projected (i.e., in the future). Among other things, this may be used to show progression of treatment.

Of course, these menu items 120-127 are merely examples. Some of these menu items may be removed, and other menu items may be added in alternative embodiments to carry out the generation and editing of the pain map and stimulation map.

The present disclosure also allows for predefined pain or stimulation regions. For example, referring now to FIG. 11, the user interface 100C shows a plurality of menu items 160-167 that each correspond to a predefined pain or stimulation region on the human body model 110. For example, in the embodiment shown, the menu item 160 may correspond to a predefined pain region in the right arm of the patient; the menu item 161 may correspond to a predefined pain region in the left arm of the patient; the menu item 162 may correspond to a predefined pain region in the waist and thighs of the patient; the menu item 163 may correspond to a predefined pain region in the abdomen of the patient; the menu item 164 may correspond to a predefined pain region in the right lower leg of the patient; the menu item 165 may correspond to a predefined pain region in the lower left leg of the patient; the menu item 166 may correspond to a predefined pain region in the right foot of the patient; and the menu item 167 may correspond to a predefined pain region in the left foot of the patient. In certain embodiments, the severity or intensity of pain/stimulation, type of pain/stimulation, and depth of pain/stimulation may be selected as a part of the predefined regions.

Figure 11:
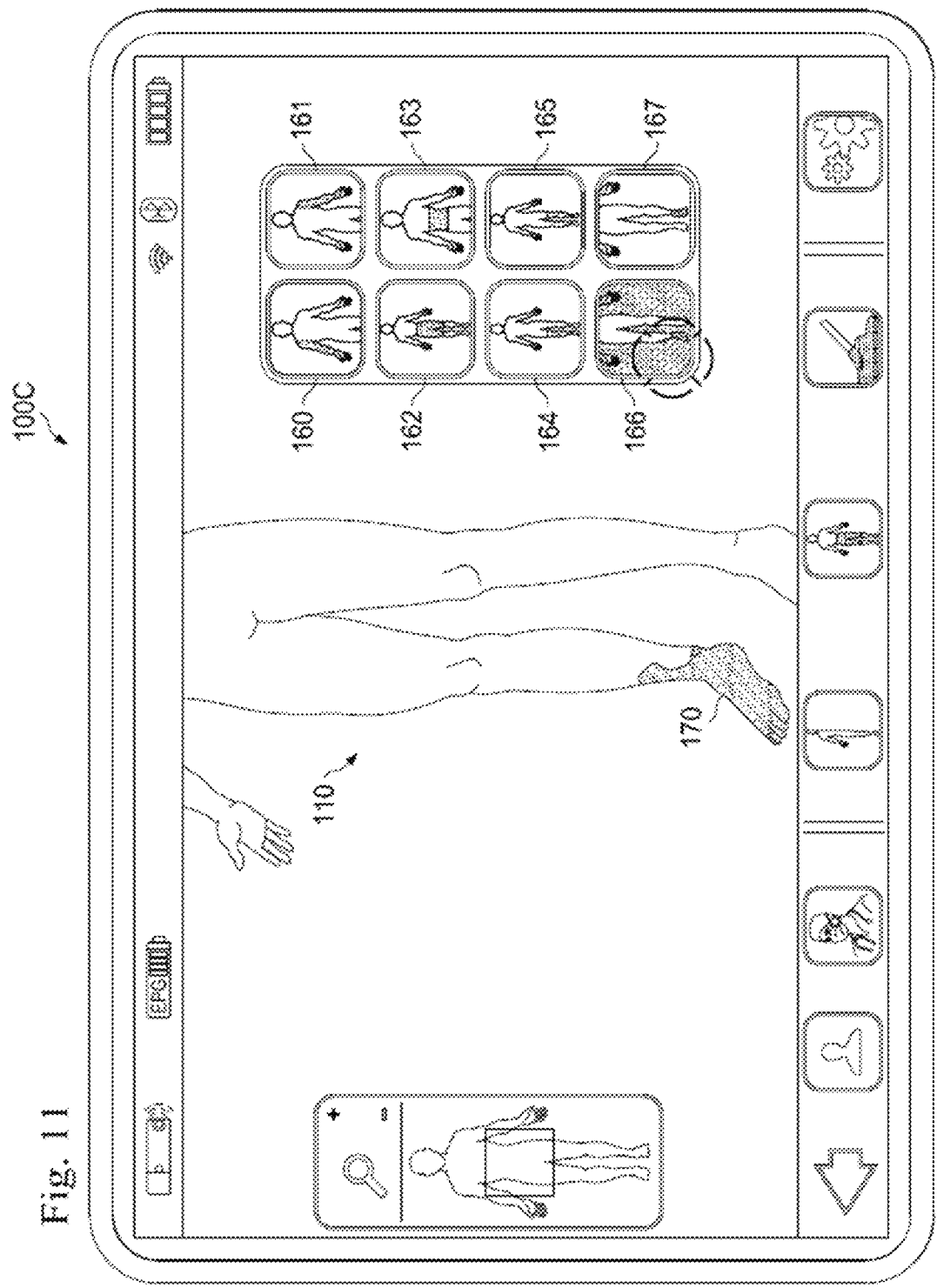

In the embodiment shown in FIG. 11, the menu item 166 is selected, which automatically generates a pain region 170 that covers the right foot of the human body model 110. The pain region 170 can then be revised by the patient to create a pain map that more accurately matches with the pain experienced by the patient. In the same manner, a predefined stimulation region may be automatically generated and then revised to create a desired stimulation map.

The correlations between stimulation parameters (e.g., milliamps, polarity, pulse width, frequency, lead position) or activity parameters (e.g., sitting, standing, sleeping, running, etc.) and perceived stimulation maps are a valuable part of map analysis, because they indicate the degree to which a parameter is related to a certain effect. Map correlations, which can be carried out between individual stimulation programs ("programs") and effective or perceived stimulation maps, are also possible between groups of programs ("programs sets") and an effective stimulation map. A more detailed discussion of stimulation parameters, programs and program sets is found in U.S. patent application Ser. No. 13/601,631, filed on Aug. 31, 2012, and entitled "Programming and Virtual Reality Representation of Stimulation Parameter Groups" to Norbert Kaula, et al., the content of which are hereby incorporated by reference in its entirety. Note that in some embodiments, the "program sets" may also be referred to as "programs" while the "programs" may be referred to as "sub-programs."

Figure 12:
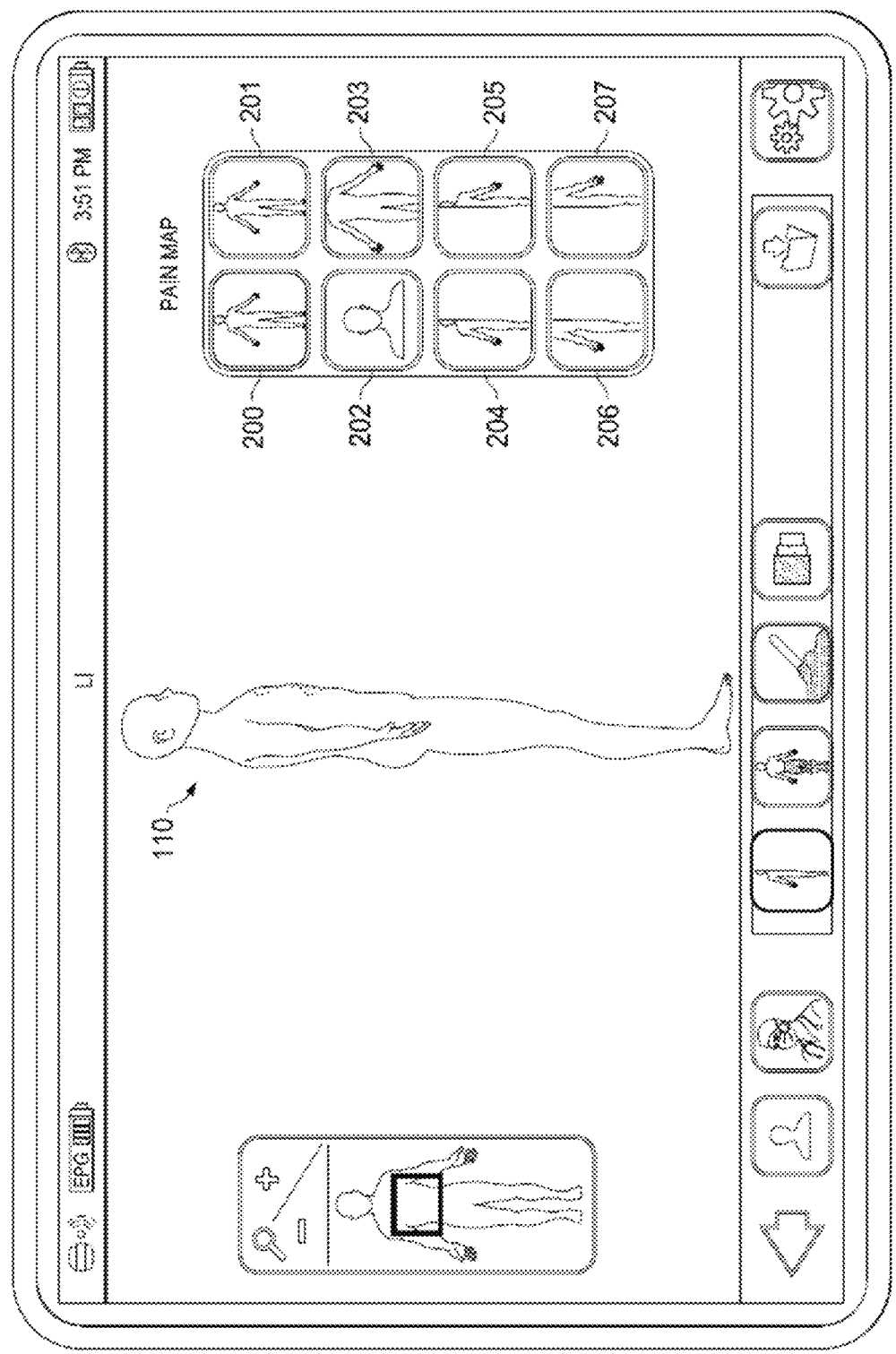
Figure 13:
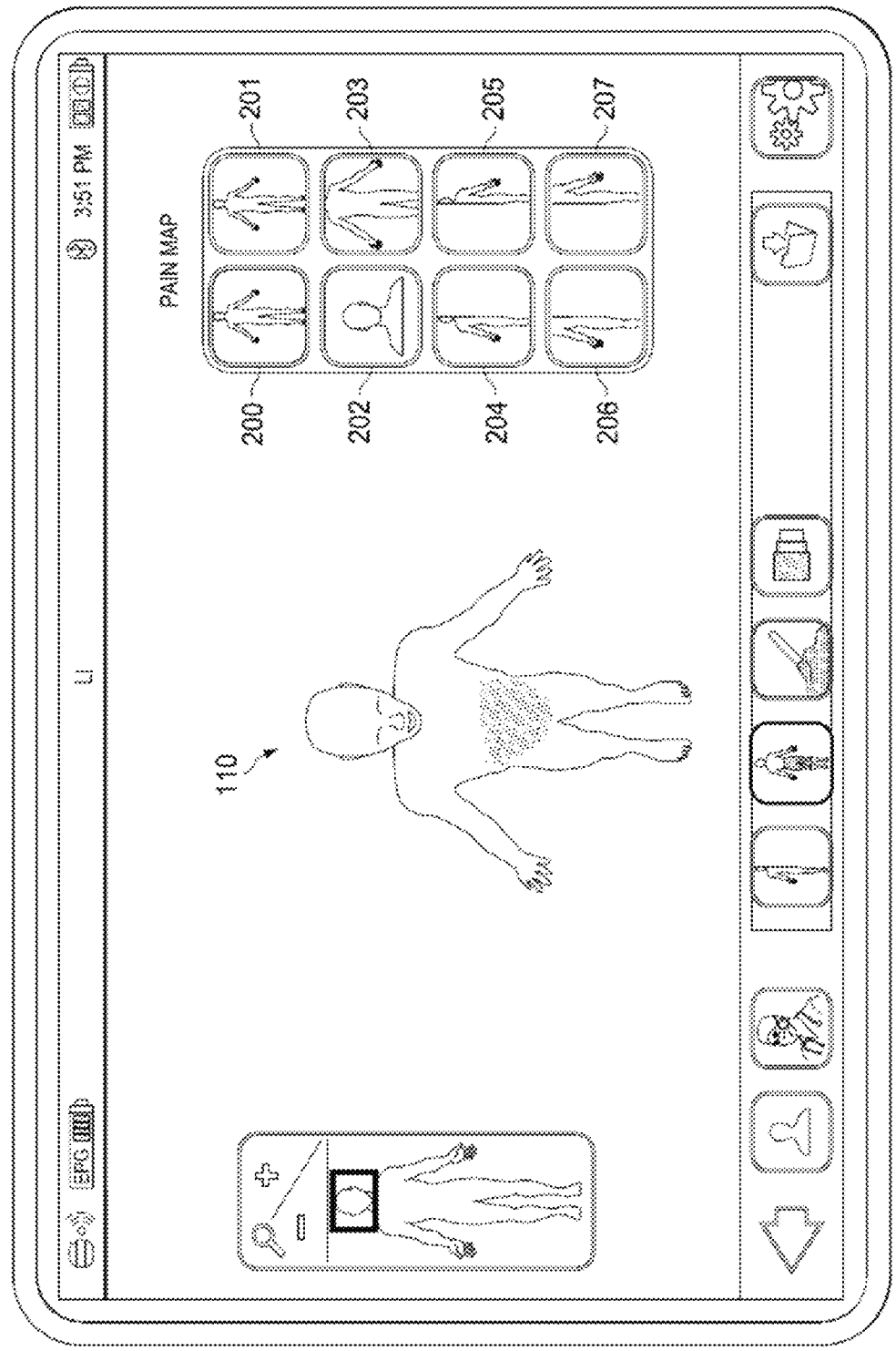

According to various aspects of the present disclosure, the human body model used to generate the pain map and stimulation map may also have a plurality of predefined starting locations for the user to choose from. FIGS. 12-13 illustrate some of these predefined starting locations as examples. As shown in FIGS. 12-13, a user interface 100D illustrates a plurality of icons 200-207. Each of the icons 200-207 corresponds to a particular portion of the human body model. As the user clicks on a particular one of the icons 200-207, the corresponding portion of the human body model will be selected as the starting locations for the human body model on which a stimulation map and/or a pain map and be drawn.

For example, as shown in FIG. 12, the icon 204 in the illustrated embodiment corresponds to the "right hand" of the human body model 110 shown in the user interface 100. In response to a user's click of the icon 204, the human body model 110 is automatically adjusted (e.g., rotated) to have the right hand of the human body model 110 face the user. In other words, the right hand of the human body model 110 is brought to the front and center of the screen for pain maps or stimulation maps to be painted thereon.

As another example, the icon 202 in the illustrated embodiment corresponds to the "head" of the human body model 110 shown in the user interface 100D. Referring to FIG. 13, in response to a user's click of the icon 202, the human body model 110 is automatically adjusted (e.g., rotated) to have the head of the human body model 110 face the user. In other words, the head of the human body model 110 is brought to the front and center of the screen for pain maps or stimulation maps to be painted thereon.

In each of the examples discussed above, a target starting location (for the generation of pain/stimulation maps) is automatically provided for the user in a quick and convenient manner. It is understood that the user may also manually manipulate the human body model 110—for example by rotating, moving, or resizing it—to arrive at a desired target starting location to generate the pain map or stimulation map. But that manual process takes more time, whereas the available predefined starting locations offer more convenience for the user and thereby make the pain/stimulation map generation process more user friendly.

According to the various aspects of the present disclosure, the clinician programmer can also provide a visualization of a migration history of the pain maps and stimulation maps. In more detail, the pain maps and stimulation maps as discussed above can be stored in an electronic memory, for example in an electronic database or another type of permanent or erasable memory storage structure. For each pain map and/or stimulation map, its respective date information (e.g., the date on which the pain map or the stimulation map is generated or created) is stored along with the pain map or stimulation map in the database. Based on such information stored in the database, a comparison between a current pain/stimulation map may be generated with an original pain/stimulation map. The comparison may include a visual coverage overlap between the two maps and/or may include a numerical value (e.g., in terms of percentages) for the increase or decrease in pain/stimulation coverage.

In some embodiments, the database resides on the clinician programmer itself. In some other embodiments, the database resides on a remote server, i.e., the cloud. In yet some other embodiments, the database resides on an implantable medical device, for example an implantable pulse generator (e.g., on the IPG 30 in FIG. 1). It is also understood that the electronic database, or a portion thereof, may be simultaneously stored in more than just one location. For example, different copies of the electronic database (or portions thereof) may be simultaneously stored in the clinician programmer, the remote server, and the implantable medical device.

Such database of pain/stimulation maps allows for a visualization of a migration history of pain maps or stimulation maps over time. For example, referring to FIGS. 14-15, the user interface 100E may display a virtual control mechanism 220 to visually indicate a pain map at a plurality of time slots in order to illustrate the migration history of the pain/stimulation map. In the illustrated embodiment, the virtual control mechanism 220 includes a slider bar 230, a marker 235 on the slider bar 230, and a virtual play button 240. The marker 235 can be moved in a horizontal direction along the slider bar 230, for example from the left of the screen toward the right, or vice versa. A length of the slider bar 230 may correspond to or represent a predefined time period, for example X years, months, weeks, or days. As such, the position of a marker 235 on the slider bar 230 corresponds to the pain/stimulation map at a particular point in time. For instance, in the illustrated embodiment, as the marker 235 is moved from the left to the right along the slider bar 230, more and more recent pain maps are retrieved from the database and displayed by the user interface 100E.

Figure 14:
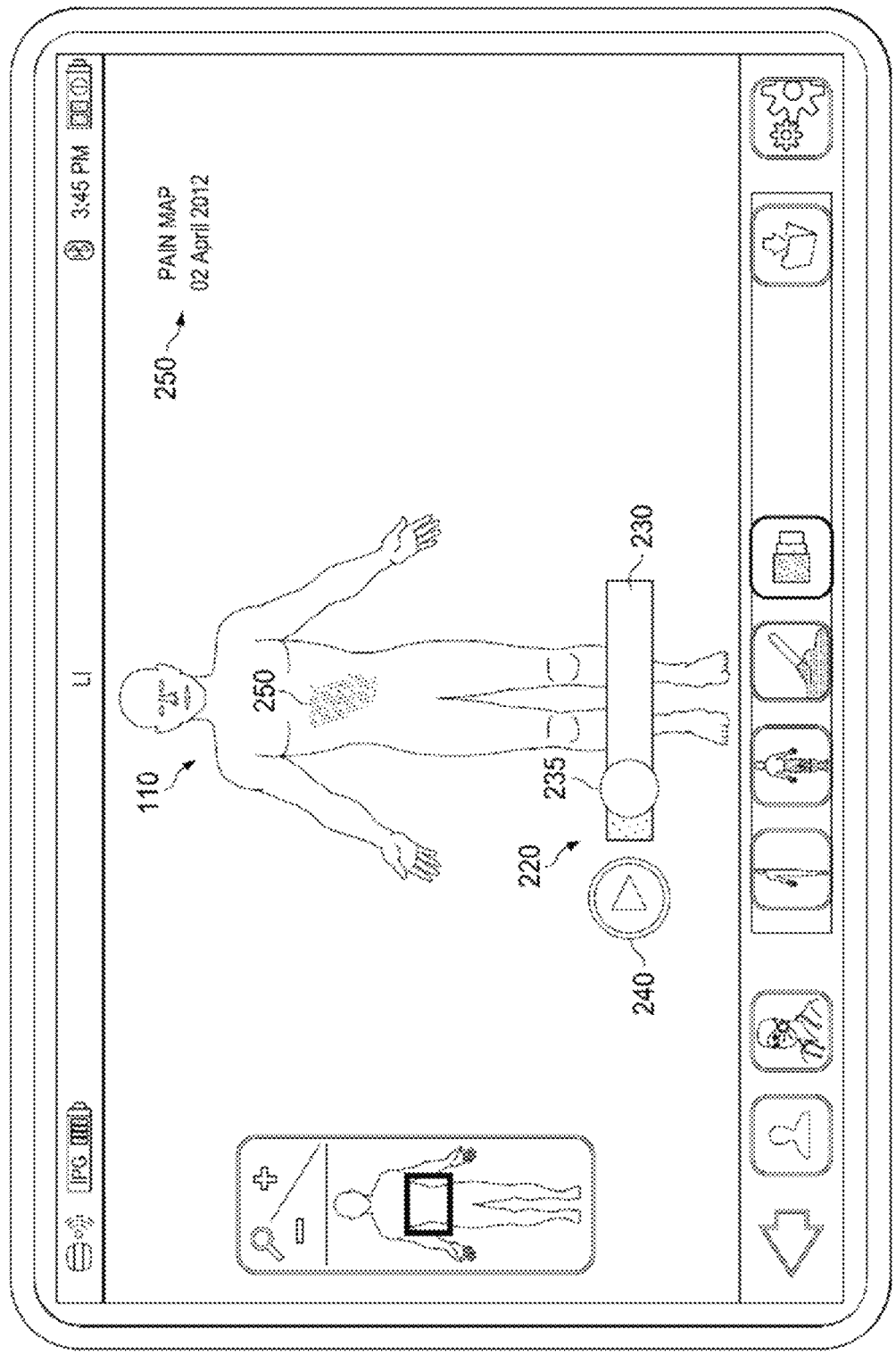
Figure 15:
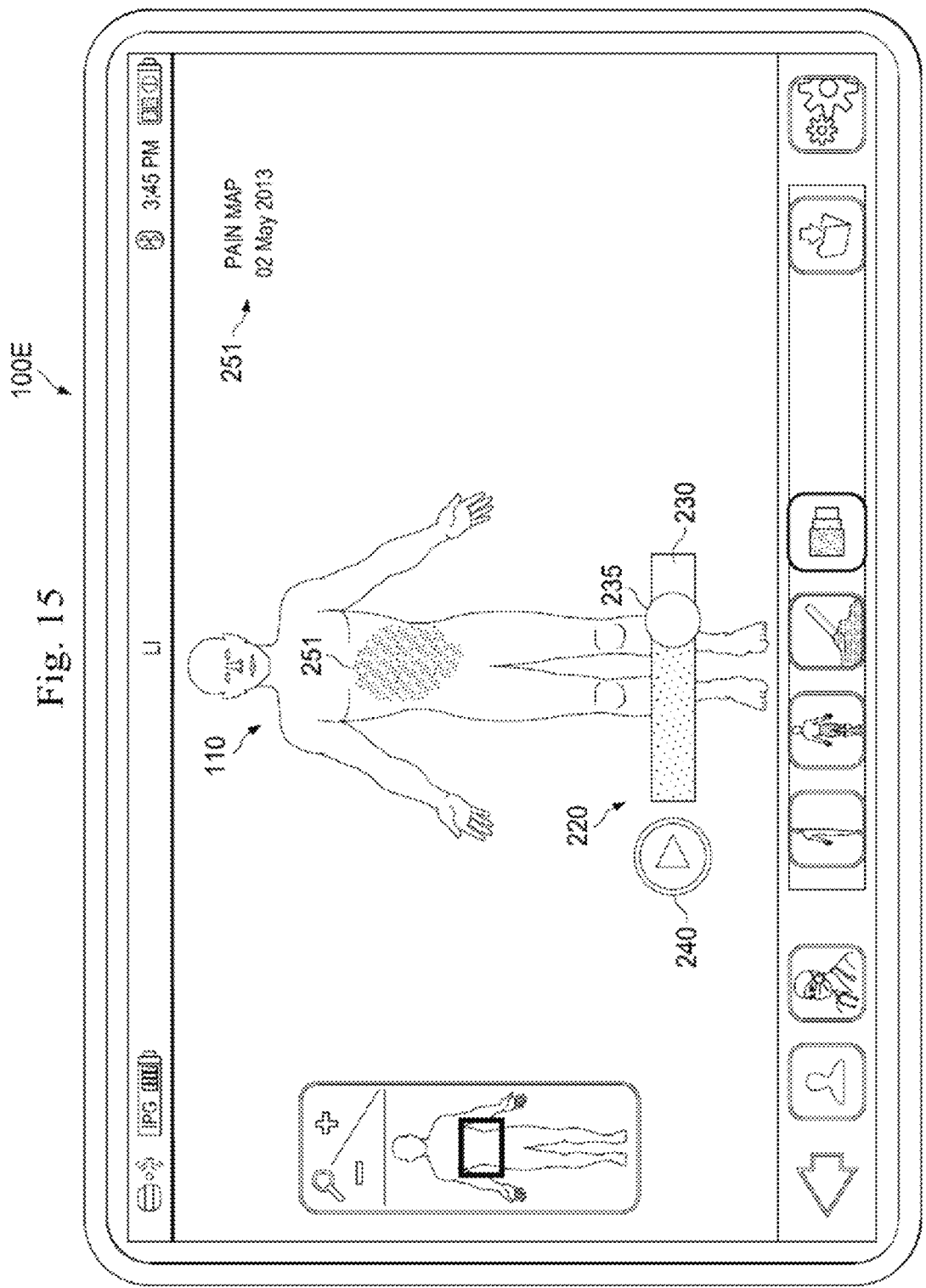

FIGS. 14-15 illustrate two example pain maps 250-251 that correspond to different points in time as the virtual control mechanism 220 is engaged. In FIG. 14, the pain map 250 is acquired or generated on Apr. 2, 2012, whereas the pain map 251 shown in FIG. 15 is acquired or generated on May 2, 2013. When the user drags the marker 235 to a first position on the slider bar 230 as shown in FIG. 14, (where the first position on the slider bar 230 corresponds to Apr. 2, 2012) the user interface 100E retrieves the pain map 250 that is captured on Apr. 2, 2012 from the database. When the user drags the marker 235 to a second position on the slider bar 230 as shown in FIG. 15, (where the second position on the slider bar 230 corresponds to May 2, 2013) the user interface 100E retrieves the pain map 251 that is captured on May 2, 2013 from the database.

A plurality of other pain maps and/or stimulation maps is stored in the electronic database discussed above in addition to the pain maps 250-251 illustrated herein. In other words, a plurality of other pain/stimulation maps may have been generated between Apr. 2, 2012 and May 2, 2013 (or before Apr. 2, 2012, and after May 2, 2013) and are stored in the electronic database, but they are not specifically illustrated herein for reasons of simplicity. Nevertheless, it is understood that as the user drags the marker 235 from the left on the slider bar 230 to the right, the user interface 100 is continuously updated with more and more recent pain maps (i.e., retrieved from the database) that are visually displayed. Similarly, if the user drags the marker 235 from the right to the left on the slider bar 230, the user interface 100 would be continuously updated with older pain maps from the past. Since the updating occurs almost instantaneously (e.g., within a fraction of a second), the user may be presented with a visual migration history of the pain/stimulation maps as the user moves the marker 235 to the left or right on the slider bar 230. Note that the user interface 100E also displays a date 250 for the pain map 250 and a date 251 for the pain map 251. The dates 250-251 may further assist the healthcare professional in making an accurate diagnosis and/or formulating a treatment plan for the patient. For example, in some embodiments, each pain map or stimulation map may be electronically associated with a particular stimulation therapy (e.g., made up of one or more stimulation programs or program sets). In this manner, if the patient reports an increase in pain when the stimulation therapy changes (e.g., from therapy 1 to therapy 2), then the healthcare professional may revert back to the old therapy (e.g., therapy 1) that offered more pain relief.

It is also understood that the user may automate the display of the migration history of pain/stimulation maps by engaging the virtual play button 240. For example, once the user clicks on the virtual play button 240, the user interface 100E will continuously display all the pain maps and/or stimulation maps that exist in the predefined time period corresponding to the length of the slider bar 230, however long that time period may be. These pain/stimulation maps may be displayed in a chronological sequence, for example from the oldest to the most recent. Each one of the pain/stimulation maps may be displayed for a predefined period of time on the screen (e.g., for one or more seconds or a fraction of a second) before the next one is displayed. Of course, the marker 235 is automatically moved along the slider bar 230 "in sync" with the display of the pain/stimulation maps, so that the position of the marker 235 is indicative of the time at which the displayed pain/stimulation map is captured throughout the automated display.

In some embodiments, the automatic display of the plurality of pain/stimulation maps in the chronological order may be performed in a manner such that it appears as a smooth time-lapse video or animation to the user. This may be done by configuring the amount of time at which each pain/stimulation map is displayed on the screen, which can be carried out by the user. In some embodiments, the animation or video will be played in its entirety in the absence of further user input. In other words, once the user presses the virtual play button 240, the animation sequence of the pain/stimulation maps will be played in its entirety (corresponding to a time period equal to the length of the slider bar 230). The user may also choose to interrupt the playing of the animation sequence by further engagements with the virtual control mechanism 220, for example pausing the playing of the animation sequence by clicking on the virtual play button 240, or reverting to manual control by clicking and dragging the marker 235 along the slider bar 230.

Based on the above discussions, it can be seen that the user can easily view and interpret the migration history of the pain/stimulation maps, which represent the change of the pain/stimulation experienced by the patient over time. The visualization of the pain/stimulation map migration history is intuitive for the user and allows him/her to formulate a more effective treatment plan for the patient accordingly. It is understood that although a single pain map (e.g., 250 or 251) is used here to visually illustrate an example migration history, stimulation maps may be superimposed on the human body model 110 along with the pain maps 250/251. In other words, the pain maps 250-251 may be simultaneously displayed with their corresponding stimulation maps (i.e., the pain map and stimulation map are obtained or generated at the same time). The simultaneous visualization of the migration history of the pain map and stimulation map further facilitates the diagnosis and treatment of the patient's pain.

Note that the virtual control mechanism 220 is used herein simply as one example for controlling the visual display of the migration history of pain/stimulation maps. In alternative embodiments, other suitable types of control mechanisms may be used, for example fast-forward or rewind buttons/arrows, or virtual toggles, switches, or dials, each of which may be used to allow the user "navigate" through time. In some other embodiments, the user may also manually enter a particular point in time and retrieve the pain/stimulation map to correspond with that time manually for display by the user interface 100E.

It is also understood that though the virtual control mechanism 220 discussed above is used in the context of a touch-sensitive user interface, it may be used in a non-touch-sensitive user interface as well. In some embodiments, the user interface may include a mouse and/or a keyboard, which may be used to engage or otherwise manipulate the virtual control mechanism 220 as well. For example, the user may use the mouse to click on the marker 235 and drag it along the slider bar 230, or use the arrow keys on the keyboard to perform the same task.

According to the various aspects of the present disclosure, the clinician programmer can also display multiple maps simultaneously or concurrently. The multiple maps may be the same type of maps (e.g., both being pain maps or both being stimulation maps), or they may be different types of maps (e.g., a pain map and a stimulation map). The simultaneous display of multiple maps also includes an overlap region between the two maps, which may allow the user (e.g., a healthcare professional) to visualize the effectiveness of a stimulation therapy.

Figure 16:
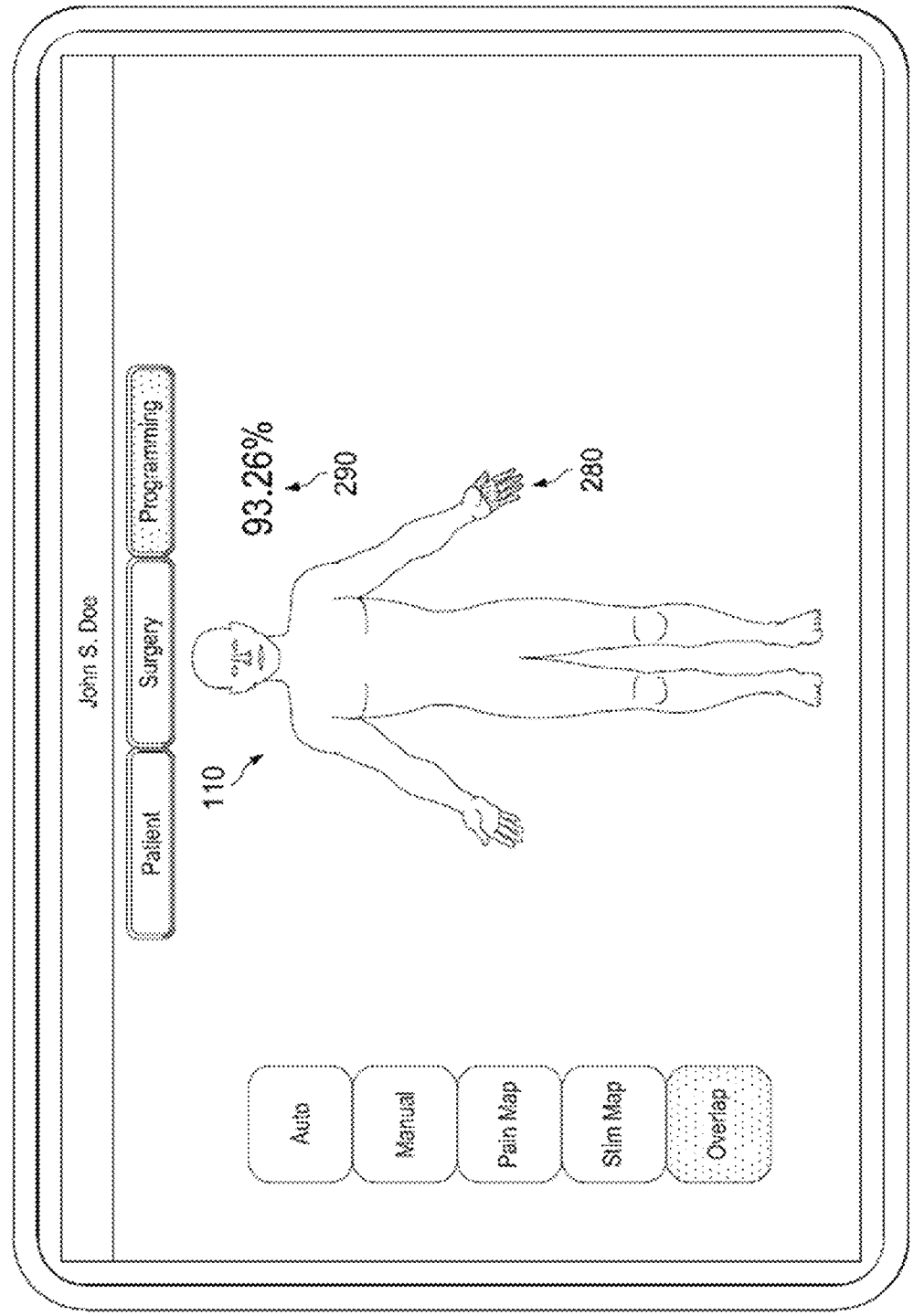

For example, referring now to FIG. 16, after a pain map and a stimulation map have been generated, a user interface 100F can be used to illustrate an overlap region 280 between the pain map and the stimulation map. The overlap region 280 is a region of the body that is covered by both the pain map (indicating that the patient feels pain in the region) and the stimulation map (indicating that the patient feels a stimulation sensation in the region). The user interface 100F also displays a numeric value 290 that represents an overlap coverage. In some embodiments, the numeric value 290 is calculated as a size of the overlap region 280 divided by a size of the pain map. Thus, the numeric value 290 may vary from 0% to 100%. In the example shown in FIG. 16, the numeric value 290 is 93.26%, which indicates that the 93.26% of the pain map is covered by the stimulation map.

It is desirable to have a close match between the pain map and the stimulation map, as that may indicate an optimal and efficient treatment (by stimulation) of the pain areas for the patient. In other words, a perfect match (e.g., 100%) between a pain map and a stimulation map indicates that every area of pain has been stimulated to provide Paresthesia in these areas, but no stimulation has been applied to areas where the patient does not feel pain. However, in real life situations, that is often not the case. Sometimes, the electrical stimulation therapy generates a stimulation sensation outside of the patient's pain areas. These "extra" areas of stimulation are unnecessary and may cause discomfort for the patient. Therefore, the clinician programmer may also visually represent such excessively stimulated areas, such as in a user interface 100G shown in FIG. 17 discussed below.

Figure 17:
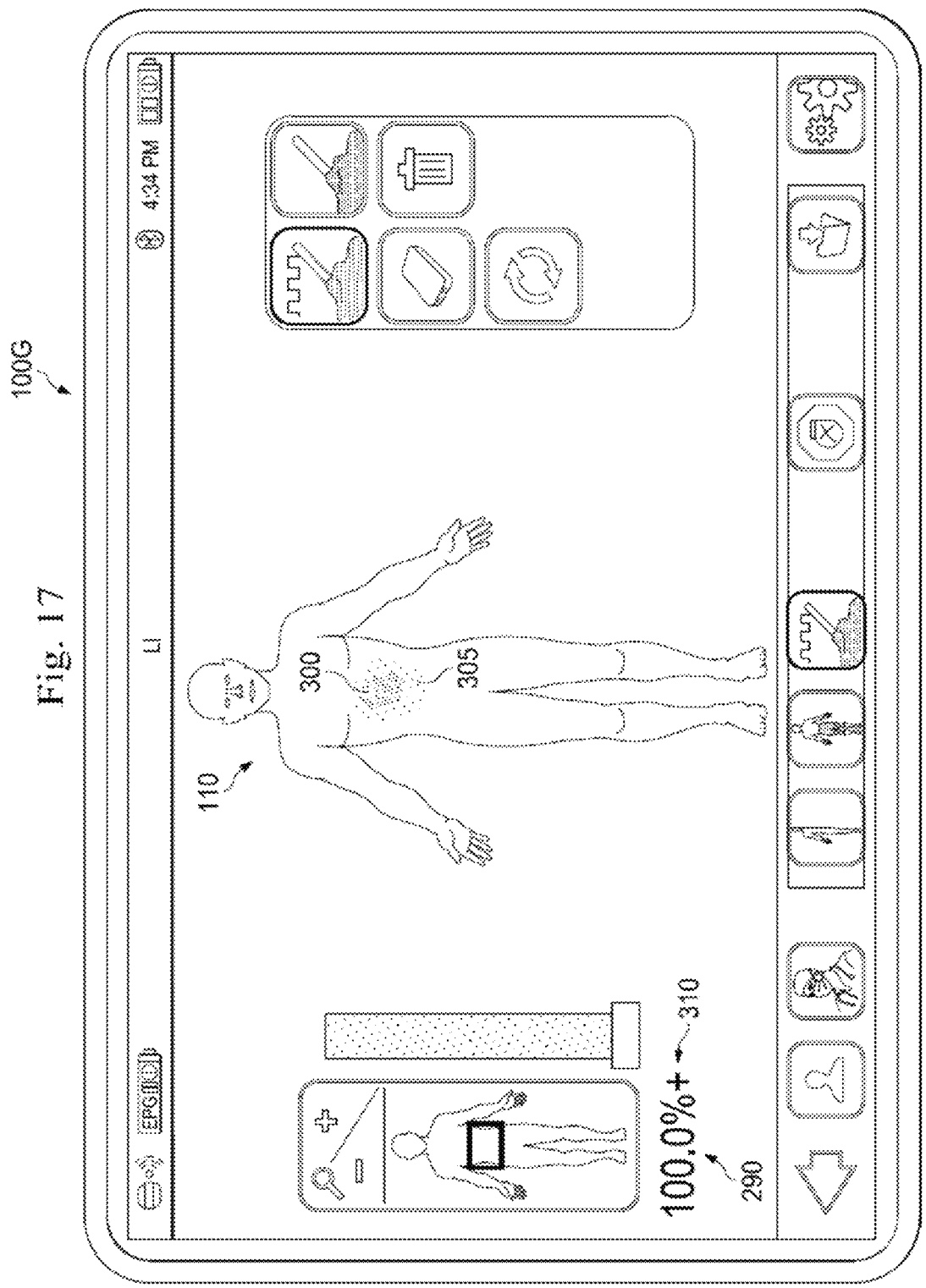

Referring to FIG. 17, the user interface 100G visually illustrates a pain map 300 and a stimulation map 305 concurrently on the human body model 110. In some embodiments, the pain map 300 and the stimulation map 305 may be given different visual characteristics, such as different colors or different types of shading, etc. In the embodiment shown in FIG. 17, the pain map 300 and the stimulation map 305 have different colors.

As can be seen in FIG. 17, the pain map 300 is also disposed entirely within, or wholly surrounded by, the stimulation map 305. Thus, the overlap region of the pain map 300 and the stimulation map 305 in this example is the same as the pain map 300 itself. Consequently, the numeric value 290 indicating the overlap coverage is 100%. However, this example does not represent a perfect match between the pain and stimulation maps, since portions of the stimulation map 305 are located outside the pain map 300. These extra or excessive areas of stimulation may cause discomfort for the patient and therefore should be minimized or reduced.

In order to make the user professional aware of the "extra" stimulation areas, the user interface 100G displays a symbol 310 next to the numeric value 290 to visually indicate the existence of excessive stimulation. In the illustrated embodiment, the symbol 310 is a "+" sign. In other embodiments, symbol 310 may be another other intuitive symbol, or even plain text indicating the existence of excessive stimulation. It is understood that excessive stimulation areas may still exist even if the overlap coverage between pain and stimulation maps is less than 100%. That is, as long as a portion of a stimulation map lies outside of a pain map, excessive stimulation exists, which may be indicated by the symbol 310.

Figure 18:
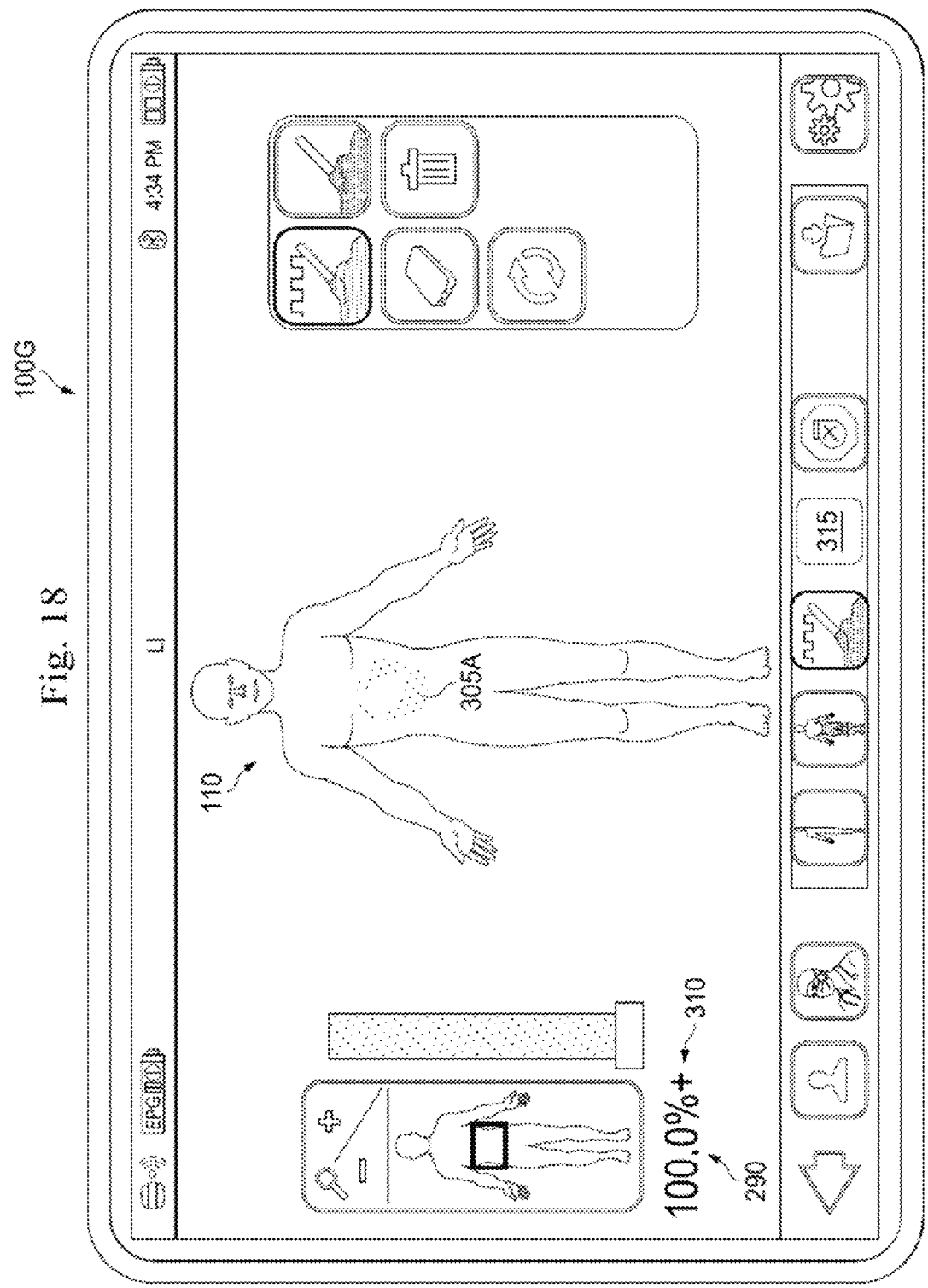

In some embodiments, the excessive stimulation areas may be selectively displayed or visually highlighted. For example, referring now to FIG. 18, a user interface 100G may be configured to "hide" the pain map 300 and the portion of the stimulation map 305 that is overlapping with the pain map 300. In other words, the user interface 100G is now only displaying a portion 305A of the stimulation map 305 that is outside the pain map 300, i.e., the area of excessive stimulation. In this manner, the user may quickly identify the excessive stimulation areas and develop plans to minimize these areas accordingly.

The selective display of the area of excessive stimulation may be performed via a suitable user input through the user interface 100G. For example, in embodiments where the user interface 100G is provided on a touch-sensitive screen, the user may double tap (with a finger or a stylus) on the excessive stimulation area 305A to selectively display it (and hide the rest of the stimulation map 305 and the pain map 300). In alternative embodiments, the user may also double tap the overlap region of the pain map 300 and the stimulation map 305 to hide it, which also allows the excessive stimulation area 305A to be selectively displayed. Of course, it is understood that the double tap may be replaced by other suitable user inputs, such as a tap-and-hold input, or a double click (or even a single click) of a mouse, or a click of a virtual button 315, which may be programed to toggle the selective display of the excessive stimulation area 305A on or off.

Figure 19:
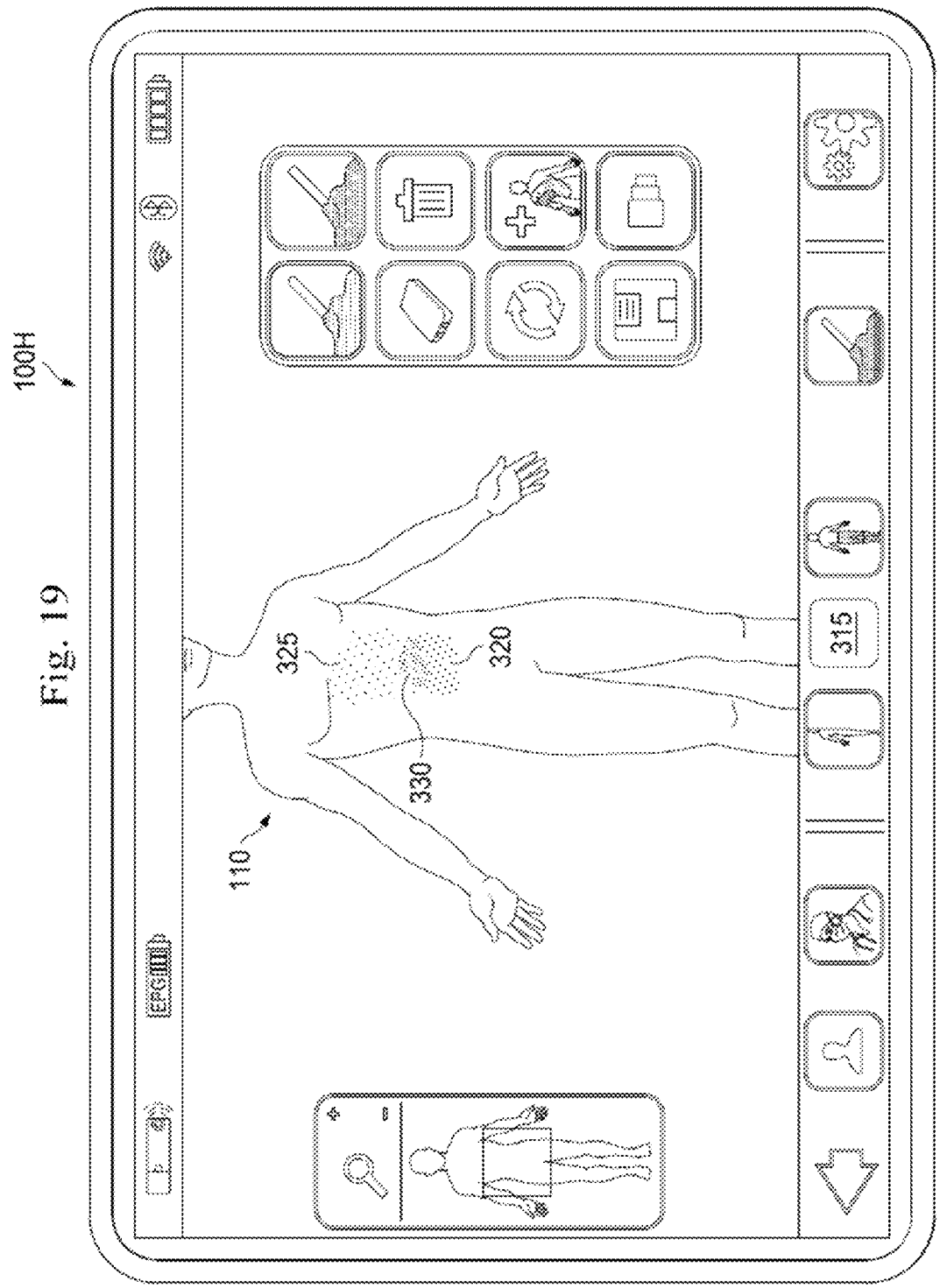

Similarly, in various other embodiments, areas of pain that are not covered by the stimulation map may also be selectively displayed or visually highlighted, for example by "hiding" the stimulation map as well as portions of the pain map that overlaps with the stimulation map. For example, referring now to FIG. 19, a user interface 100H illustrates an example pain map 320 and an example stimulation map 325 on the human body model 110. The pain map 320 and the stimulation map 325 have an overlap region 330 (i.e., covered by both the pain map 320 and the stimulation map 325). It can be seen that the overlap region 330 in this embodiment is represented by a color that is a mix of the colors of the pain map 320 and the stimulation map 325.

Figure 20:
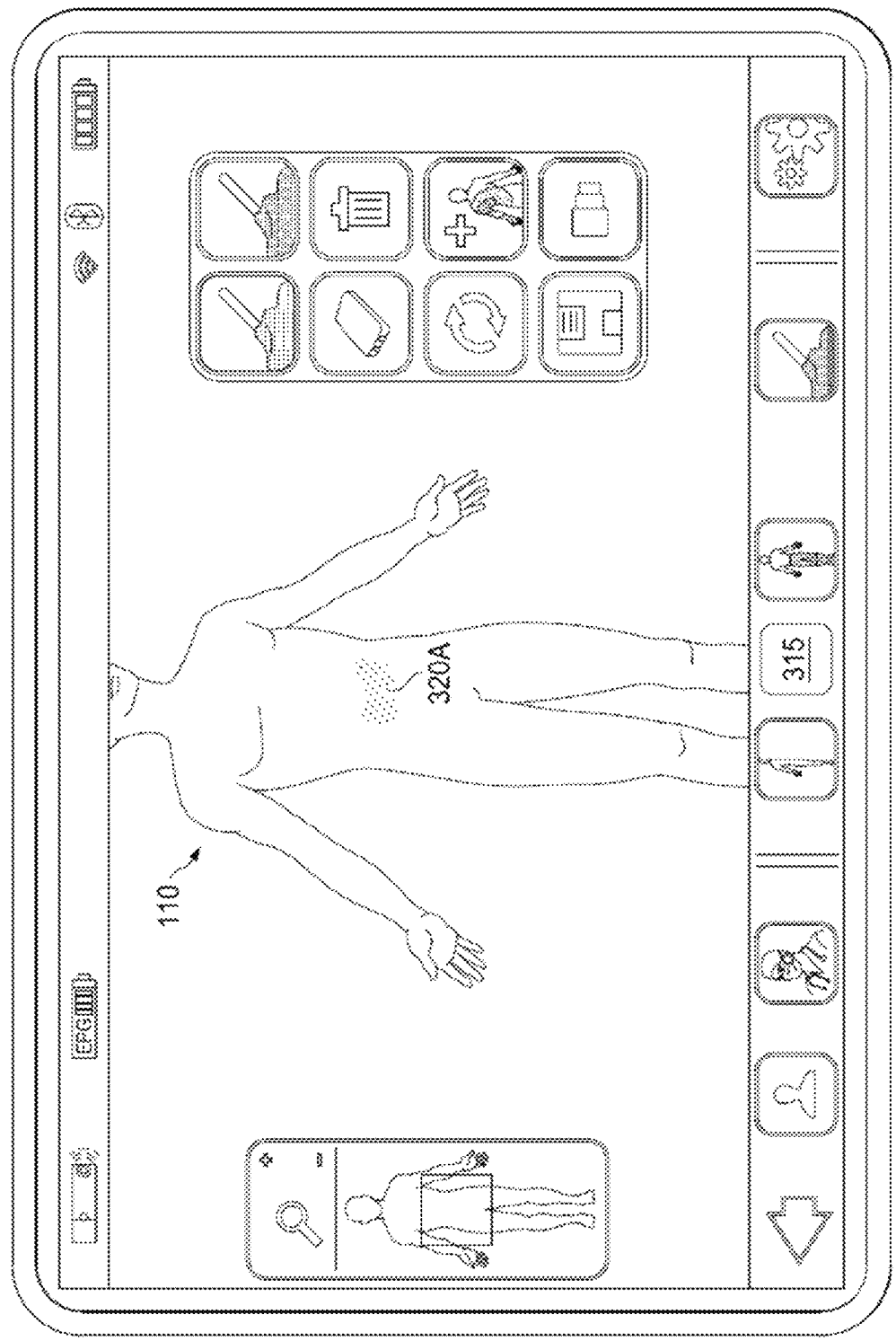

Referring now to FIG. 20, in response to a suitable user engagement with the user interface 100H, a portion 320A of the pain map 320 that is not covered by the stimulation map 325 may be selectively displayed. Stated differently, the rest of the pain map 320 as well as the stimulation map 325 may be hidden in response to the user engagement. In this manner, the user may quickly identify the pain areas that still need to be treated, and accordingly the user may develop plans to provide stimulation coverage for such inadequately stimulated areas. Again, the user engagement may be a double tap, a single tap, a tap-and-hold, a single click or a double click of the mouse, or a click of the virtual button 315, etc. Conversely, this suitable user engagement may also be performed to selectively display a portion of the stimulation that is not overlapping with a pain map. In other words, the excess stimulation areas may be identified in this manner, so that the user may determine how to configure or adjust the stimulation parameters to reduce the excess (unwanted) stimulation.

Figure 21:
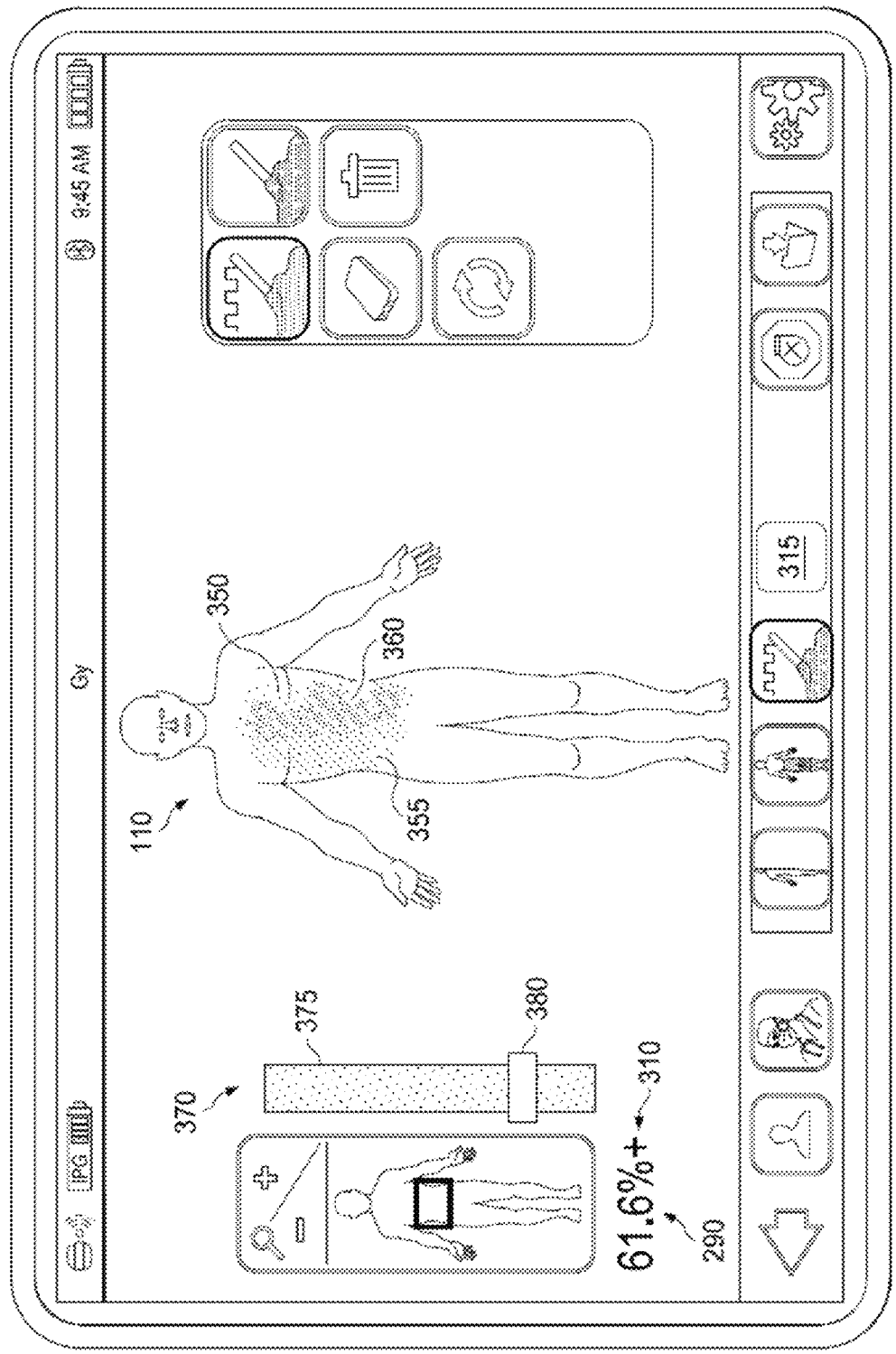
Figure 22:
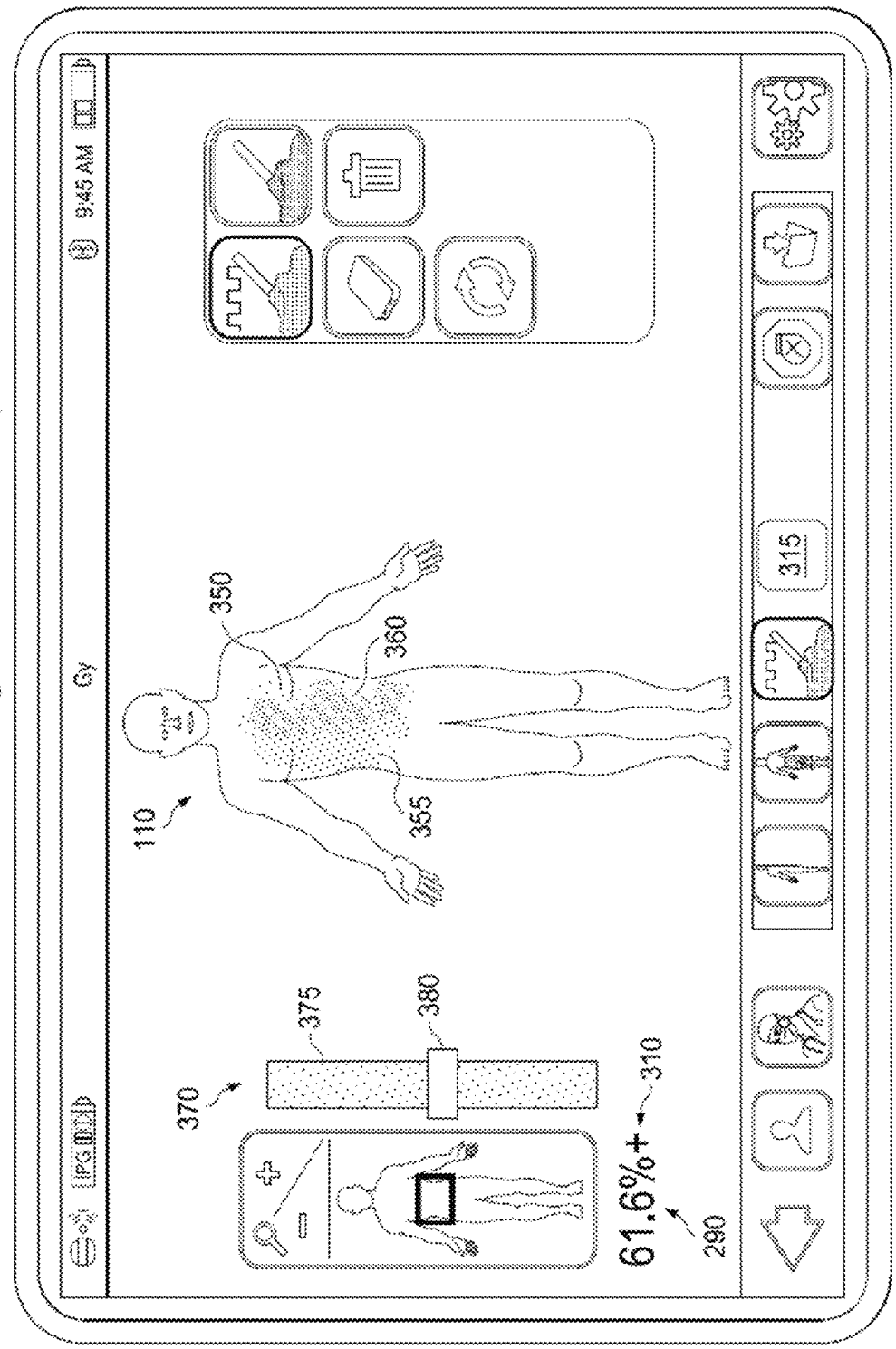

According to various aspects of the present disclosure, the pain and stimulation maps may also be weighted differently. Referring now to FIGS. 21-22, a user interface 100I displays on the human body model 110 a pain map 350, a stimulation map 355, and an overlap region 360 of the pain map 350 and the stimulation map 355. As discussed above, the user interface 100I may display an overlap coverage as a numeric value 290, which in this case is 61.6%. In the illustrated embodiment, the numeric value 290 may be calculated by dividing a size of the overlap region 360 of the pain and stimulation maps by a size of the pain map 350. Also, since a portion of the stimulation map 355 lies outside the pain map 350, it indicates the presence of excessive stimulation, which is represented by the display of the symbol 310 (e.g., "+" sign).

In some embodiment, the weighting of the pain map 350 and the stimulation map 355 may include visually emphasizing one of these maps while simultaneously de-emphasizing the other. For example, the pain map 350 and the stimulation map 355 may each have an adjustable transparency level (or opaqueness level). By simultaneously adjusting the respective transparency levels of the pain map 350 and the stimulation map 355 in opposite manners, the pain map 350 may be visually emphasized by decreasing its transparency level, while the stimulation map 355 may be visually de-emphasized by increasing its transparency level, or vice versa.

To carry out the simultaneous adjustment of the respective visual emphasis of the pain map 350 and the stimulation map 355, the user interface 100I may utilize a virtual control mechanism 370 that can be engaged by the user. In the embodiment shown in FIGS. 21-22, the virtual control mechanism 370 includes an elongate slider bar 375 and a marker 380 that can be moved along the slider bar 375 in response to a user engagement. For example, the marker 380 may be dragged along the slider bar 375 via a touch-sensitive input in some embodiments, or via a mouse or a keyboard (e.g., arrow keys) input in alternative embodiments. As the marker 380 moves along the slider bar 375 in an upward direction, the transparency level of the pain map 350 decreases, and the transparency level of the stimulation map 355 increases. In this manner, the pain map 350 is visually emphasized while the stimulation map 355 is visually de-emphasized. Conversely, as the marker 380 moves along the slider bar 375 in a downward direction, the transparency level of the pain map 350 increases, and the transparency level of the stimulation map 355 decreases. In this manner, the pain map 350 is visually de-emphasized while the stimulation map 355 is visually emphasized.

Using FIGS. 21-22 as an example, it can be seen that the position of the marker 380 is located near a bottom end of the slider bar 375 in FIG. 21, which corresponds to a more transparent pain map 350 and a more opaque stimulation map 355. In FIG. 22, the marker 380 has been moved up along the slider bar 375, which corresponds to a more opaque pain map 350 (i.e., less transparent) and a more transparent stimulation map 355. As such, it can be seen that the movement of the marker 380 along the slider bar 375 may be used to fade into one of the pain and stimulation maps 350 and 355 and out of the other. This affords the user (e.g., a healthcare professional) diagnostic versatility and flexibility, which may allow the user to quickly develop an effective treatment therapy for the patient.

In some embodiments such as the one illustrated in FIGS. 21-22, in addition to (or instead of) changing the respective transparency levels of the pain and stimulation maps 350 and 355, the engagement of the virtual control mechanism 370 may change the visual characteristics of the pain and stimulation maps 350 and 355 in other ways. For example, the movement of the marker 380 along the slider bar 375 may change the respective colors of the pain and stimulation maps 350 and 355, (e.g., darken the color of one of them while lighten the color of the other). In some embodiments, as the coloring of the pain and stimulation maps 350 and 355 changes along with the movement of the marker 380, the coloring of the overlap region 360 may also be adjusted accordingly. In addition, in some embodiments such as the one illustrated in FIGS. 21-22, the movement of the marker 380 also changes the visual characteristic (e.g., color or shading) of the slider bar 375 itself. For example, as the marker 380 is moved in a direction that increases the visual emphasis of the pain map 350, the color of the slider bar 375 may shift to more closely match the color of the pain map 350 (and less of the color of the stimulation map), and vice versa.

In some embodiments, the adjustment of the visual emphasis of the pain and stimulation maps 350 and 355 may be performed such that only a portion (rather than an entirety) of these maps is visually emphasized or de-emphasized. For example, as the marker 380 moves in a given direction along the slider bar 375, the visual emphasis increases for only the portion of the pain map 350 that is not covered by the stimulation map 355, while the visual emphasis decreases for only the portion of the stimulation map 355 that is not covered by the pain map 350. In other words, the increase or decrease of the visual emphasis may only apply to the map regions outside the overlap region 360. Alternatively, the increase or decrease of the visual emphasis may only apply to the overlap region 360 as the marker 380 moves along the slider bar 375.

Figure 23:
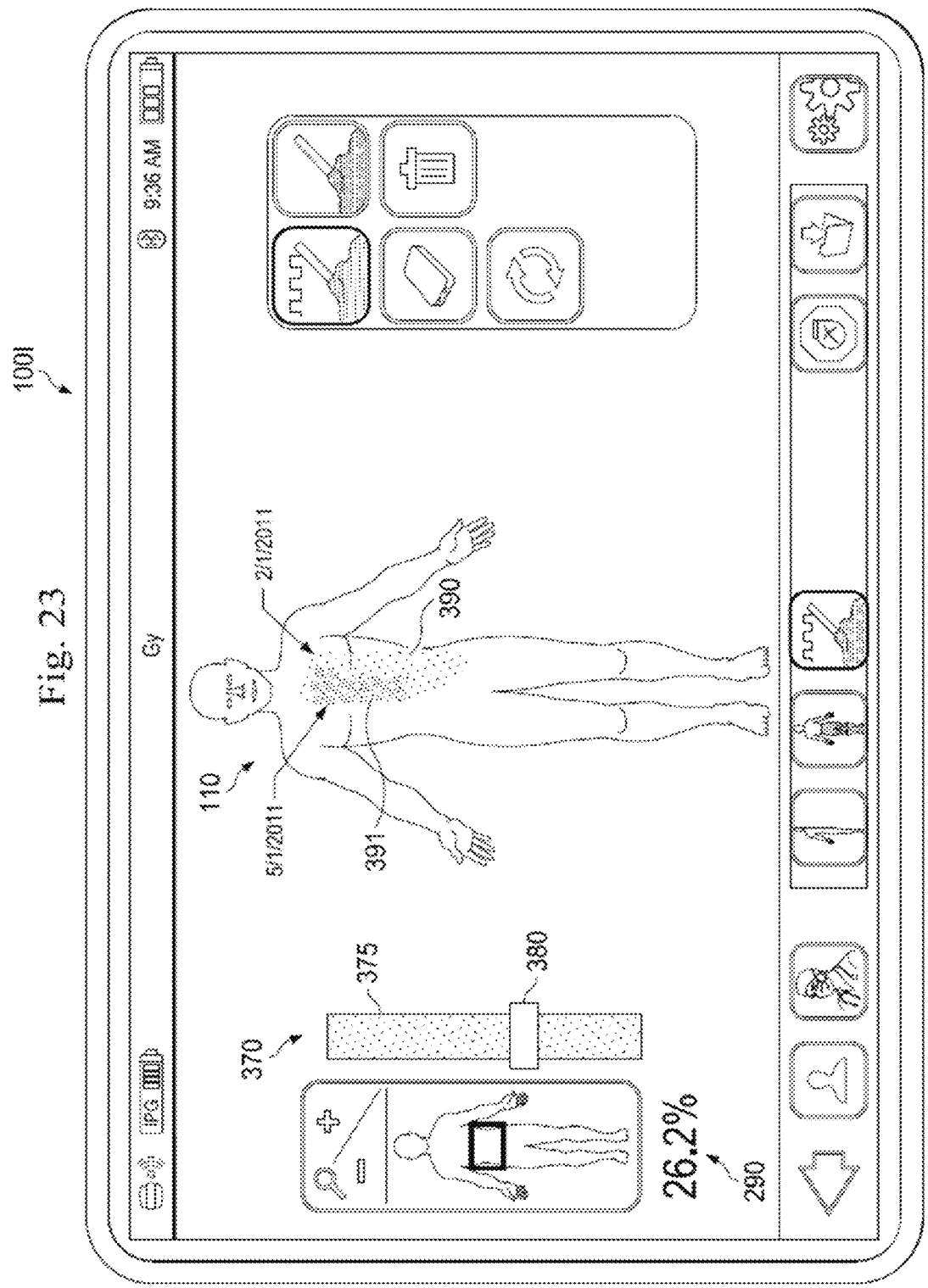

It is understood that although the examples discussed above pertain to the visual emphasis adjustment of a pain map and a stimulation map, the same concept may be applied to two (or more) maps of the same type. For example, referring now to FIG. 23, two pain maps 390 and 391 are concurrently displayed on the human body model 110. The two pain maps 390-391 are visually differentiated from one another in a similar manner as the pain map 350 and the stimulation 355 discussed above, for example with different colors. In the illustrated embodiments, the pain maps 390-391 are pain maps that are acquired from different points in time. For example, the pain map 390 is acquired on Feb. 1, 2011, and the pain map 391 is acquired on Apr. 1, 2011. These dates may be displayed alongside their respective pain maps 390-391. In other embodiments, the pain maps 390-391 may be maps that are associated with different treatment protocols (e.g., pain maps created in response to different stimulation programs, which may be around the same point in time). In yet other embodiments, the pain maps 390-391 may be pain maps that belong to different patients. In a similar manner, two or more stimulation maps may be displayed concurrently on the human body model 110. The concurrent display of two or more pain maps 390-391 or two or more stimulation maps (and the corresponding overlap region between the two maps) offers the user additional medical information that can be used to develop a treatment therapy for the patient.

It is also understood that the virtual control mechanism 370 illustrated herein is merely an example, and it may be implemented differently in other embodiments and still provide the same or similar functions discussed above. For example, the slider bar 375 may be horizontal rather than vertical, and it may be curved or rounded (e.g., in the shape of an arc or a semi-circle) rather than having a straight profile or a rectangular shape. As another example, the virtual control mechanism 370 may be implemented with interactive virtual buttons, such as arrow buttons that correspond to different directions, where the engagement of one of such arrows will increase the visual emphasis of one of the maps while decreasing the other. As yet another example, the virtual control mechanism 370 may be implemented as a virtual toggle, where the toggle can be pressed in a given direction (or the other) to increase the visual emphasis of one of the maps while decreasing the other. As a further example, the virtual control mechanism 370 may be implemented as a virtual dial, where the dial can turned/twisted/wound in a specific manner to increase the visual emphasis of one of the maps while decreasing the other. As one more example, the virtual control mechanism 370 may be implemented as an alphanumeric input field, where the user can enter a number (or adjust an existing number) that corresponds to a specific respective visual emphasis of each of the displayed maps.

Figure 24:
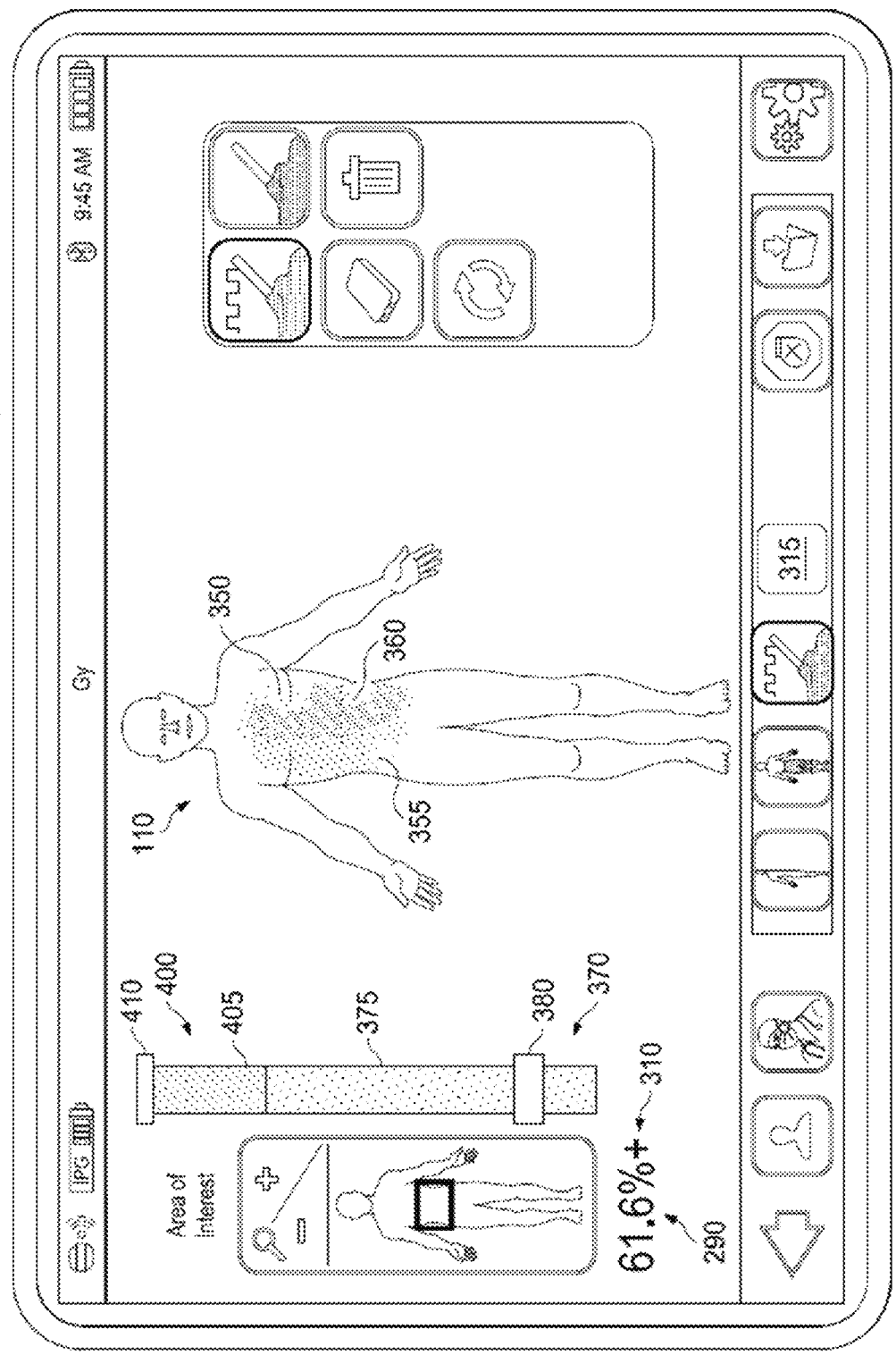

The present disclosure also allows the display and visual emphasis adjustment for one or more predefined regions on the human body model 110, for example areas that are more important for pain management. Referring to FIG. 24, a user interface 100J may display another virtual control mechanism 400. In the embodiment illustrated, the virtual control mechanism 400 includes another slider bar 405 that is similar to the slider bar 375, as well as another marker 410 that is similar to the marker 380. In other words, the marker 410 may be moved along the slider bar 405 as well. Alternatively, the slider bar 405 may be "joined" with the slider bar 375 such that the marker 380 may move onto the slider bar 405, in which case the marker 410 may be eliminated. As such, the virtual control mechanism 400 may be considered a part of the virtual control mechanism 370 as well.

Figure 25:
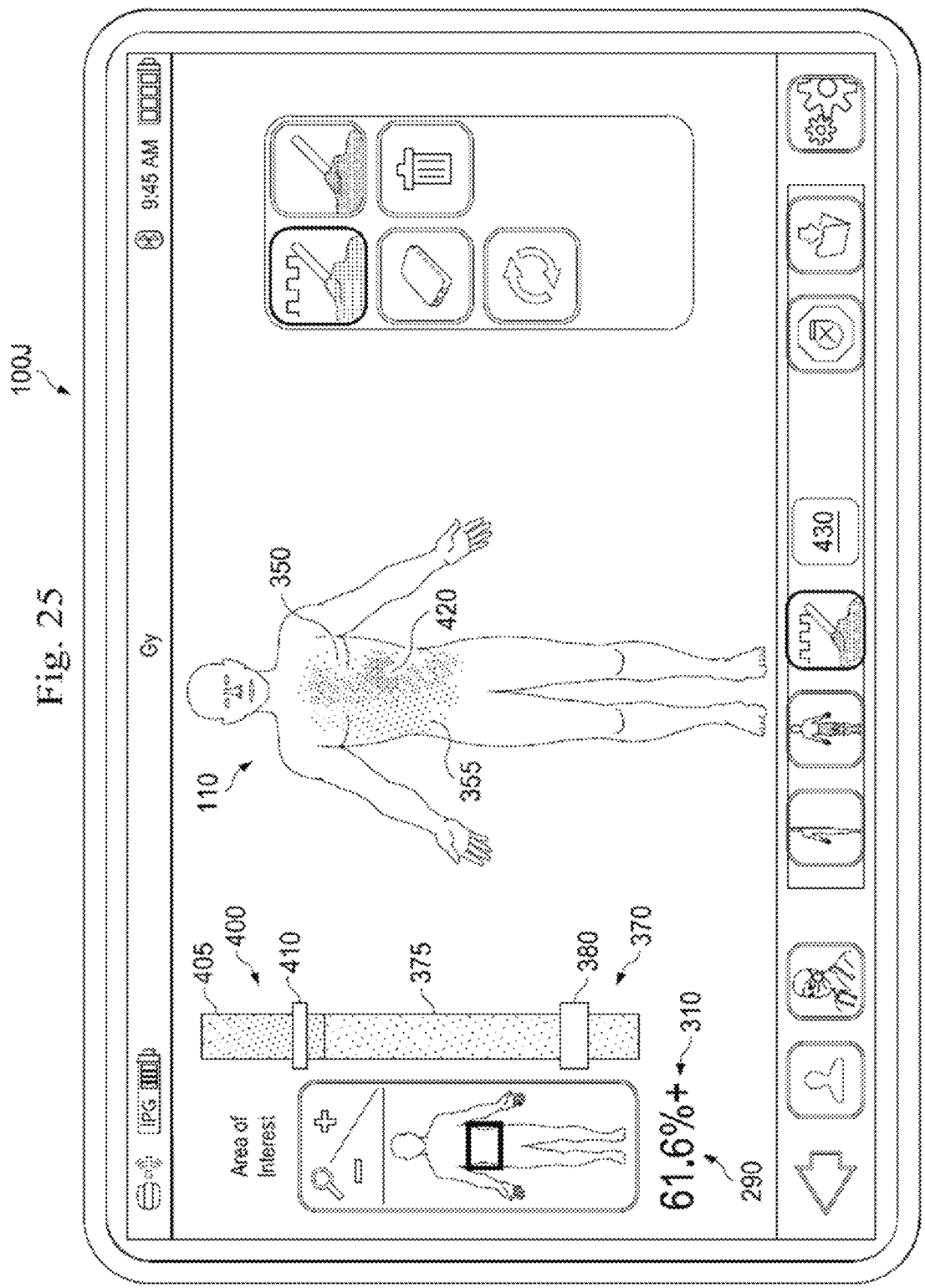

Referring now to FIG. 25, when the marker 380 moves along the slider bar 400, the visual emphasis of an area of interest 420 may be adjusted accordingly. In more detail, the area of interest 420 may be an area of pain or area of stimulation that is important. For example, the area of interest 420 may be a particularly painful area, or an area of stimulation that is particularly helpful in providing pain relief. The patient or the user may have previously defined this area of interest 420. At a later time, it is possible that the area of interest 420 may become obfuscated or "lost in the shuffle" when the various pain and stimulation maps are displayed on the human body model 110. For example, the area of interest 420 is hardly visible in FIG. 24, which may correspond to a location of the marker 410 being at a top of the slider bar 405. The poor visibility of the area of interest 420 may be due to a high visual emphasis of the stimulation map 355. In FIG. 25, as the marker 410 is moved toward a bottom direction along the slider bar 405, the predefined area of interest 420 is brought into focus progressively, i.e., its visual emphasis increases. Again, the visual emphasis increase or decrease of this area of interest 420 may be accomplished by adjusting the transparency level, the color, or the shading of the area of interest 420.

By visually emphasizing the area of interest 420, the user can be reminded of areas that are important for pain management and treatment, which may allow the user to develop more accurate and effective treatment therapies. It is also understood that the virtual control mechanism 400 is provided merely as an example to illustrate how the area of interest 420 may be displayed and have its visual emphasis adjusted. In alternative embodiments, virtual buttons, toggles, dials, etc. may also be used to accomplish the same tasks. For example, a virtual button 430 may be used to selectively turn on or off the area of interest 420.

Figure 26:
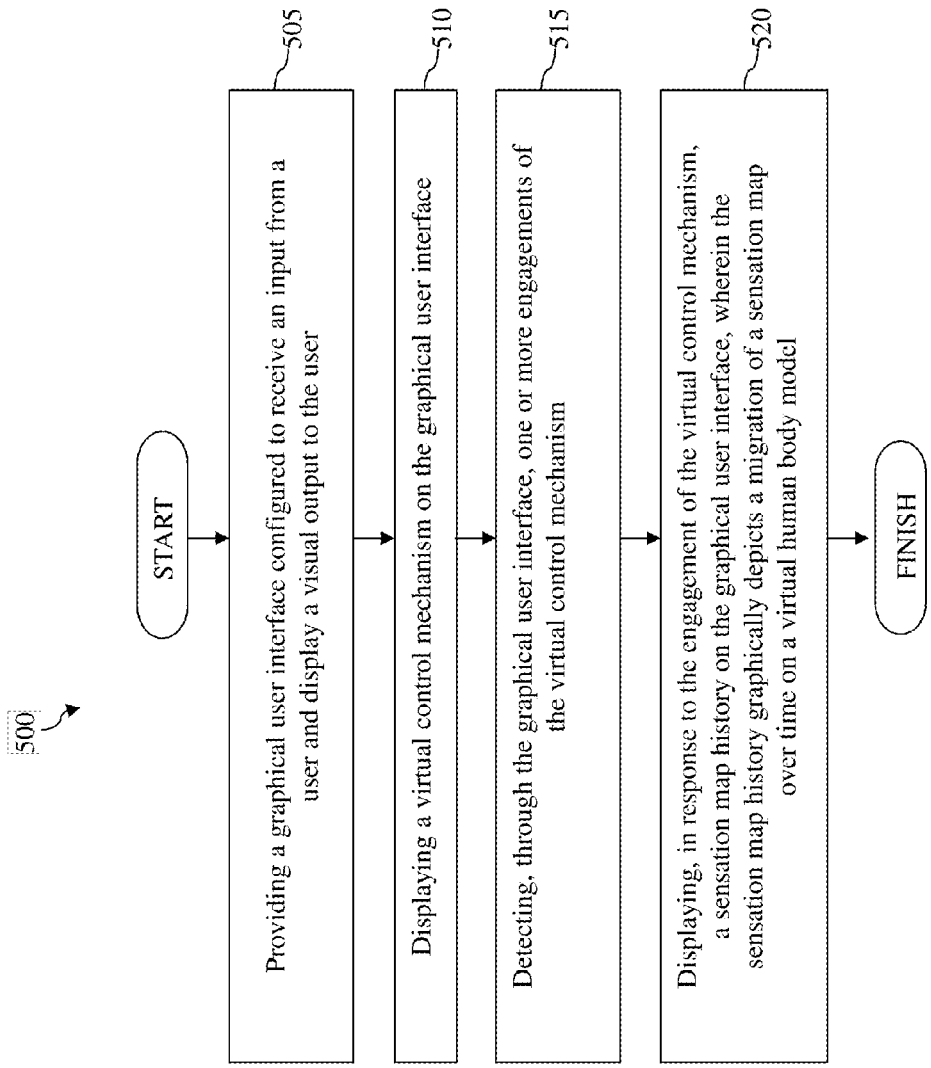
FIGS. 26-27 are flowcharts illustrating different example methods of generating and displaying pain/stimulation maps according to various embodiments of the present disclosure.

FIG. 26 is a flowchart illustrating a method 500 of visualizing a sensation experienced by a patient. The method 500 may be performed by an electronic device, such as by one or more electronic processors of a clinician programmer. The method 500 includes a step 505 of providing a graphical user interface configured to receive an input from a user and display a visual output to the user. In some embodiments, the graphical user interface may include a touchscreen. In other embodiments, the graphical user interface may include a keyboard, a mouse, or other suitable input/output devices.

The method 500 includes a step 510 of displaying a virtual control mechanism on the graphical user interface. In some embodiments, the displaying of the virtual control mechanism comprises displaying a slider bar and a marker configured to be moved along the slide bar, wherein a length of the slider bar corresponds to a predefined period of time.

The method 500 includes a step 515 of detecting, through the graphical user interface, one or more engagements of the virtual control mechanism. The virtual control mechanism may include a slider bar, a marker that can be moved along the slider bar, and a virtual play button. In some embodiments, the detecting of the one or more engagements of the virtual control mechanism comprises detecting a movement of the marker along the slider bar.

The method 500 includes a step 520 of displaying, in response to the engagement of the virtual control mechanism, a sensation map history on the graphical user interface. The sensation map history graphically depicts a migration of a sensation map over time on a virtual human body model. In some embodiments, the step 520 includes displaying at least one of: a pain map and a stimulation map. In some embodiments, the displaying of the sensation map history comprises automatically updating the sensation map history in response to the detected movement of the marker along the slider bar. In some embodiments, the updating of the sensation map history is performed such that the sensation map history is updated to correspond with the detected movement of the marker along the slider bar in real time. In some embodiments, the displaying of the sensation map history comprises playing an animation sequence of a plurality of sensation maps. The sensation maps each graphically depicts a sensation experienced by the patient at a different point in time. In some embodiments, the playing of the animation sequence comprises displaying the plurality of sensation maps in a chronological order or in a reverse chronological order.

In some embodiments, the step 515 of detecting of the one or more engagements of the virtual control mechanism comprises detecting a press of the virtual button, in which case the playing of the animation sequence in step 520 comprises automatically playing, in response to the detected press of the virtual button, the animation sequence in its entirety in an absence of further user input.

It is understood that additional process steps may be performed before, during, or after the steps 505-520 discussed above. For example, in some embodiments, the method 500 may include a step of storing a plurality of sensation maps in a memory. The sensation maps each graphically depicts a sensation experienced by the patient at a different point in time. The method 500 may also include a step of retrieving at least a subset of the plurality of sensation maps from the memory. In some embodiments, the step of storing of the sensation maps comprises storing respective date information to be associated with each of the sensation maps, and the step of displaying the sensation map history comprises displaying the respective date information associated with each of the sensation maps. In some other embodiments, the method 500 may include a step of sending the sensation map history to a remote server for a comparative analysis. The sending of the sensation map history may include removing private information of the patient associated with the sensation map history. Additional steps may be performed by the method 500, but they are not specifically discussed herein for reasons of simplicity.

Figure 27:
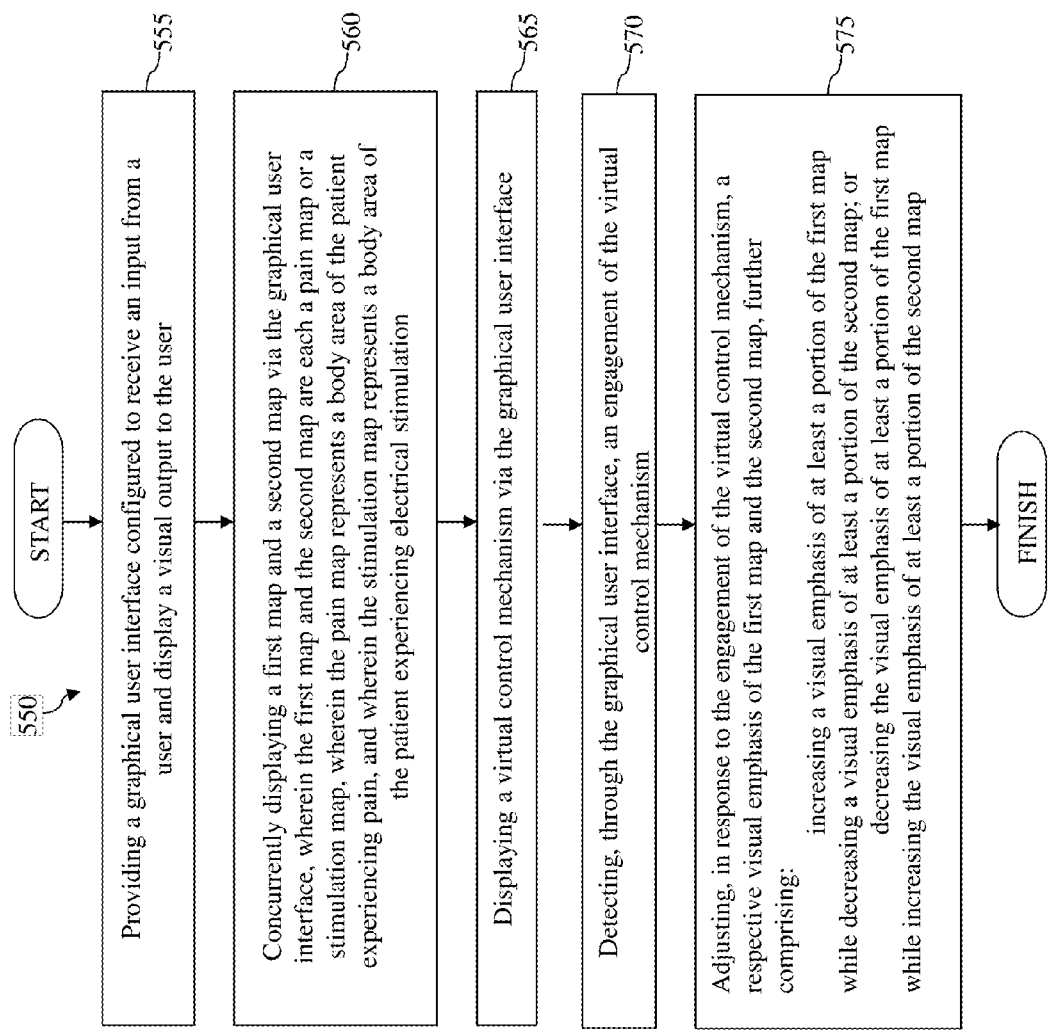

FIG. 27 is a flowchart illustrating a method 550 of displaying pain or stimulation experienced by a patient. The method 550 may be performed by an electronic device, such as by one or more electronic processors of a clinician programmer. The method 550 includes a step 555 of providing a graphical user interface configured to receive an input from a user and display a visual output to the user. In some embodiments, the graphical user interface may include a touchscreen. In other embodiments, the graphical user interface may include a keyboard, a mouse, or other suitable input/output devices.

The method 550 includes a step 560 of concurrently displaying a first map and a second map via the graphical user interface. The first map and the second map are each a pain map or a stimulation map. The pain map represents a body area of the patient experiencing pain. The stimulation map represents a body area of the patient experiencing electrical stimulation. In some embodiments, the first map is a pain map, and the second map is a stimulation map. In some embodiments, the concurrent display of the first map and the second map comprises displaying an overlap region between the first map and the second map. In some embodiments, the step 560 may further include a sub-step of displaying a numerical value that indicates a size of the overlap region relative to a size of one of: the first map and the second map. In some embodiments, the step 560 may include a sub-step of displaying a sign if a portion of the stimulation map lies outside of the pain map. In some embodiments, the increasing or decreasing of the visual emphasis is only applied to the overlap region.

In other embodiments, the first map and the second map are the same type of maps. For example, they may both be pain maps, or they may both be stimulation maps. The same type of maps may be acquired from different points in time, or acquired in response to different stimulation programs, or acquired from different patients.

The method 550 includes a step 565 of displaying a virtual control mechanism via the graphical user interface. In some embodiments, the step 565 may include displaying an elongate slider bar and a marker configured to be moved along the slide bar. The detecting of the one or more engagements of the virtual control mechanism comprises detecting a movement of the marker along the slider bar in one of a first direction and a second direction different from the first direction. The increasing of the visual emphasis of at least a portion of the first map and the decreasing of the visual emphasis of at least a portion of the second map are performed in response to a detected movement of the marker along the slider bar in the first direction. The decreasing of the visual emphasis of at least a portion of the first map and the increasing of the visual emphasis of at least a portion of the second map are performed in response to a detected movement of the marker along the slider bar in the second direction.

The method 550 includes a step 570 of detecting, through the graphical user interface, an engagement of the virtual control mechanism.

The method 550 includes a step 575 of adjusting, in response to the engagement of the virtual control mechanism, a respective visual emphasis of the first map and the second map. The step 575 may further include the following steps: increasing a visual emphasis of at least a portion of the first map while decreasing a visual emphasis of at least a portion of the second map; or decreasing the visual emphasis of at least a portion of the first map while increasing the visual emphasis of at least a portion of the second map.

It is understood that additional process steps may be performed before, during, or after the steps 555-575 discussed above. For example, in some embodiments, the method 550 may include a step of adjusting a visual emphasis of a predefined region of one of the first and second maps. For example, the predefined region may include an area of interest that is important for pain management or treatment. Additional steps may be performed by the method 550, but they are not specifically discussed herein for reasons of simplicity.

Figure 28:
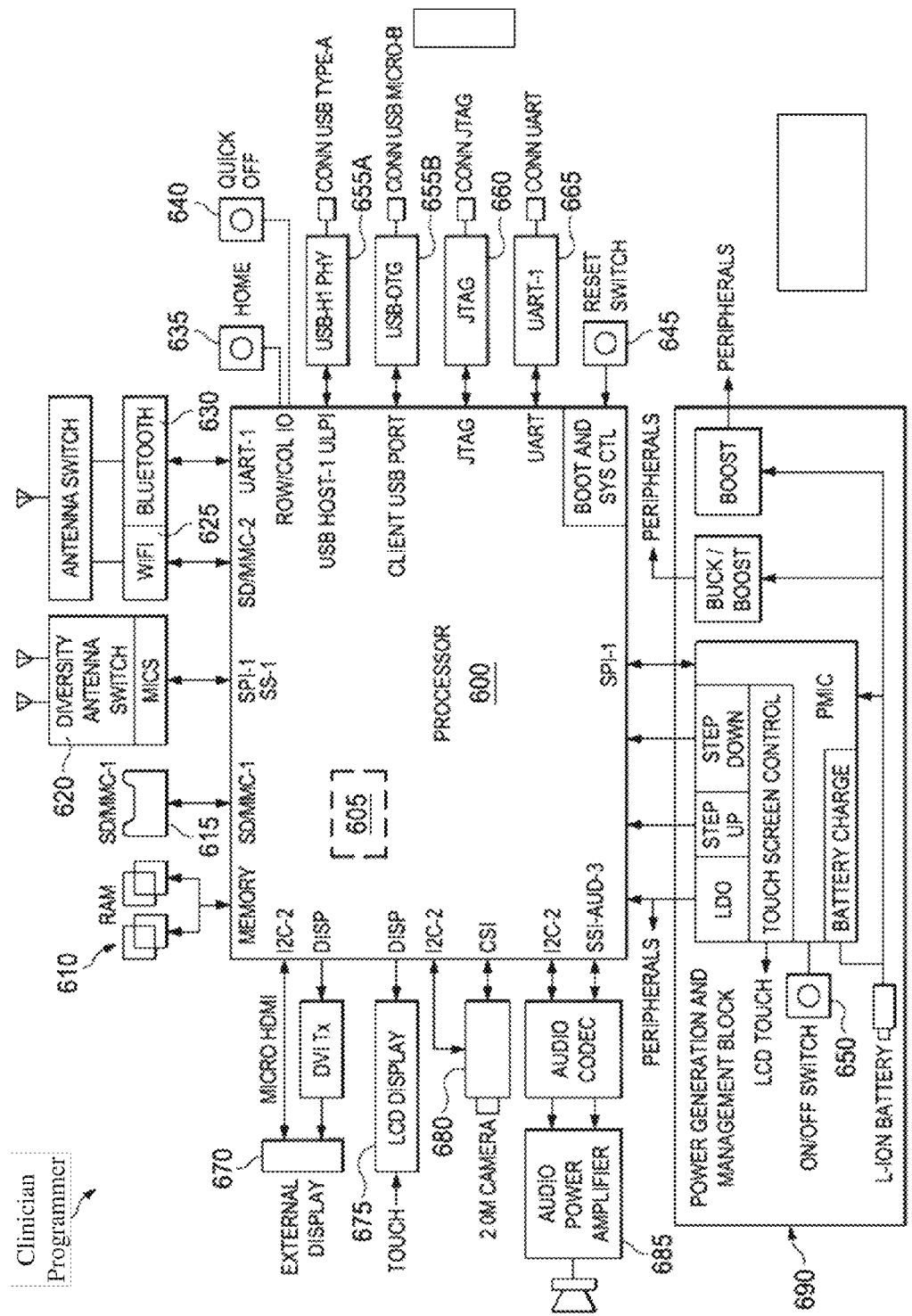
FIG. 28 is a simplified block diagram of an electronic programmer according to various embodiments of the present disclosure.

FIG. 28 shows a block diagram of one embodiment of the electronic programmer (CP) discussed herein. For example, the electronic programmer may be a clinician programmer (CP) configured to generate and display the migration history of pain/stimulation maps, or the concurrent display of two or more maps (e.g., pain and stimulation maps or multiple maps of the same type) discussed above. It is understood, however, that alternative embodiments of the electronic programmer may be used to perform these tasks as well.

The CP includes a printed circuit board ("PCB") that is populated with a plurality of electrical and electronic components that provide power, operational control, and protection to the CP. With reference to FIG. 28, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 28 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 28.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 28.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 28) may also be included for data transfer.

It is understood that a patient programmer may be implemented in a similar manner as the clinician programmer shown in FIG. 28.

Figure 29:
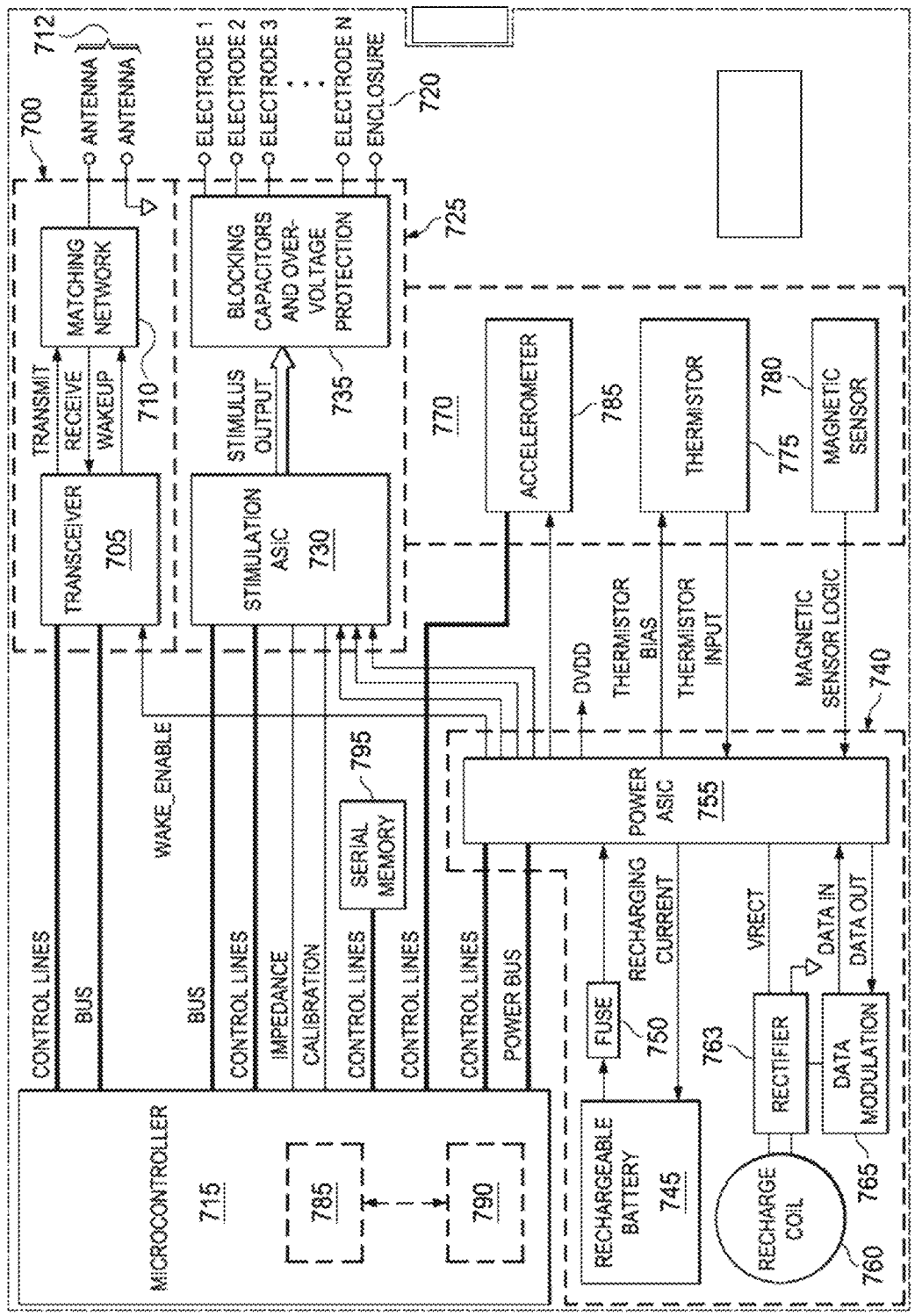
FIG. 29 is a simplified block diagram of an implantable medical device according to various embodiments of the present disclosure.

FIG. 29 shows a block diagram of one embodiment of an implantable medical device. In the embodiment shown in FIG. 29, the implantable medical device includes an implantable pulse generator (IPG). The IPG includes a printed circuit board ("PCB") that is populated with a plurality of electrical and electronic components that provide power, operational control, and protection to the IPG. With reference to FIG. 29, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 29, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 29 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 30:
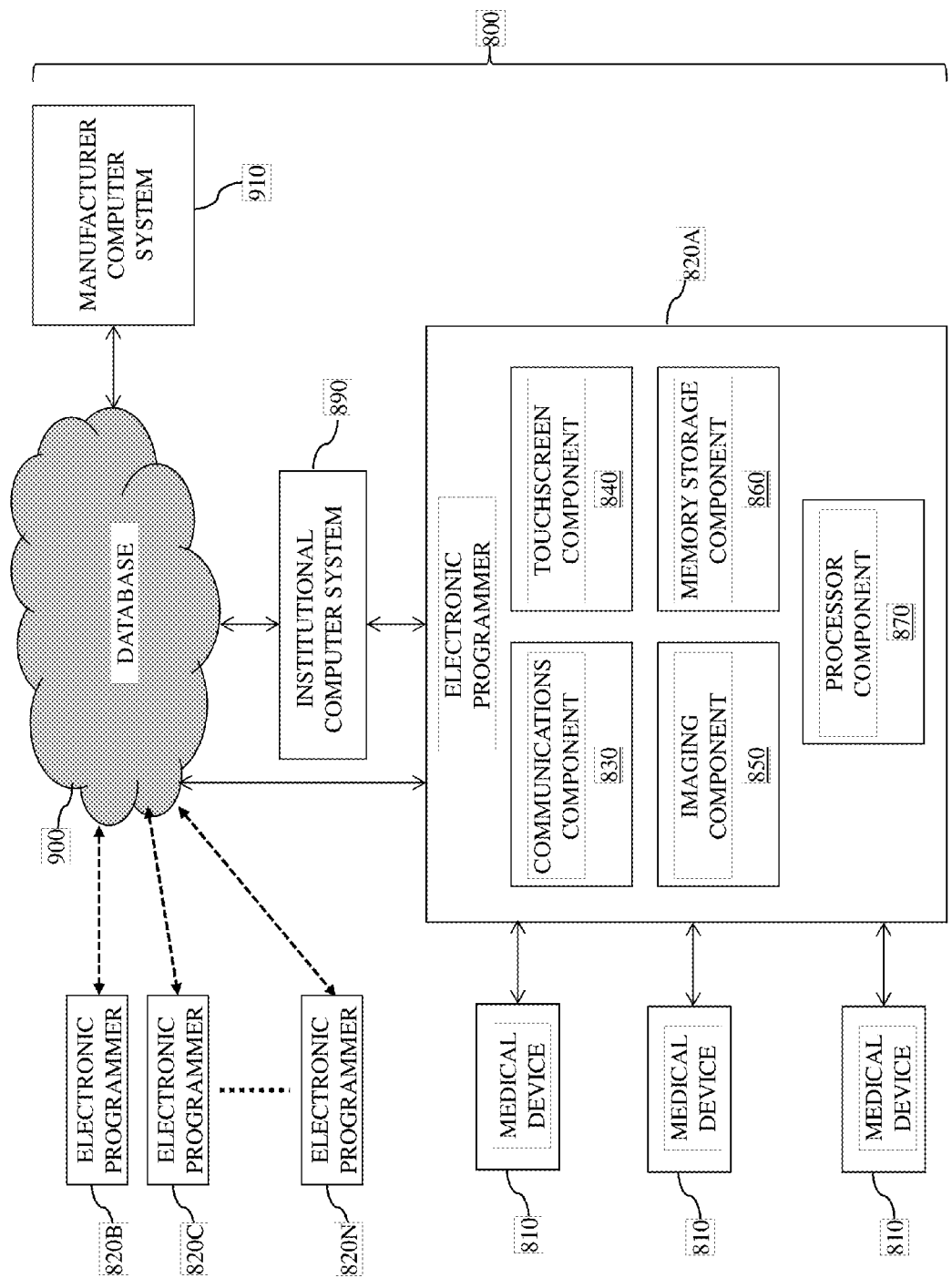
FIG. 30 is a simplified block diagram of a medical system/infrastructure according to various embodiments of the present disclosure.

Referring now to FIG. 30, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 29), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 28. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with (or instead of) the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joysticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 30 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, the pain/stimulation maps may be uploaded from the electronic programmer 820A to the database 900. The pain/stimulation maps saved in the database 900 may thereafter be downloaded by any of the other electronic programmers 820B-820N communicatively coupled to it, assuming the user of these programmers has the right login permissions. For example, a 2D pain/stimulation map may be generated by the electronic programmer 820A and uploaded to the database 900, as discussed in detail in U.S. patent application Ser. No. 13/973,219, filed on Aug. 22, 2013, entitled "Method and System of Producing 2D Representations of 3D Pain and Stimulation Maps and Implant Models on a Clinician Programmer," to Norbert Kaula, et al., the disclosure of which is hereby incorporated by reference in its entirety. That 2D pain/stimulation map can then be downloaded by the electronic programmer 820B, which can use the downloaded 2D pain/stimulation map to reconstruct or recreate a 3D pain/stimulation map. In this manner, a less data-intensive 2D pain/stimulation map may be derived from a data-heavy 3D pain/stimulation map, sent to a different programmer through the database, and then be used to reconstruct the 3D pain/stimulation map. It is understood that the pain/stimulation map migration history discussed above with reference to FIGS. 14-15 or the concurrently displayed maps discussed above with reference to FIGS. 16-25 may also be sent to the database 900 for storage.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

The system 800 allows for comparative analysis to be conducted based on the pain/stimulation map migration history discussed above with reference to FIGS. 14-15. For example, the migration history of the pain/stimulation maps may be gathered from a plurality of patients via the electronic programmers 820A-820N. The privacy information of these patients is stripped or removed. For example, the patient's name, address, phone number, or employ may be removed to comply with Health Insurance Portability and Accountability Act (HIPPA) rules. Other relevant non-sensitive patient information (e.g., patient's physiological profile such as gender, height, or weight, or even medical history) may be retained if permitted by HIPPA. In this manner, a plurality of anonymous pain/stimulation map migration histories may be stored, for example in the database 900, along with certain types of patient information as discussed above.

A healthcare professional may thereafter download these conglomerated pain/stimulation migration histories and/or send them to a remote server for analysis. The remote server may include the database 900, the institutional computer system 890, the manufacturer computer system 910, or another suitable remote server not illustrated herein. In some situations, the analysis may detect certain pain/stimulation migration trends, which may be associated with their respective patient's physiological characteristics or medical histories. Based on this trend information, the healthcare professional may be able to better diagnose or treat his/her patient.

As an example, supposed the current patient is a 40-year old white male who is 6 feet tall and weighs 200 pounds, and who has had a knee replacement performed in the past few years due to a sports-related injury. The healthcare professional treating this patient may scour the database 900 to see if there are any close matches for this particular patient's profile. If one or more close matches are identified, their associated pain map migration histories may be retrieved. The healthcare professional may study these pain map migration histories, which are for patients similar to the current patient. Based on this information, the healthcare professional may be able to estimate with more accuracy how this particular patient's pain is likely to evolve or migrate over time. Accordingly, the healthcare professional may be able to formulate a treatment plan that is not only targeted toward this patient's current pain symptoms, but also directed to how this patient's pain is likely to evolve in the future. In this manner, the pain/stimulation map migration histories may be used to aid the healthcare professional in diagnosing and treating his/her current patient.

Figure 31A:
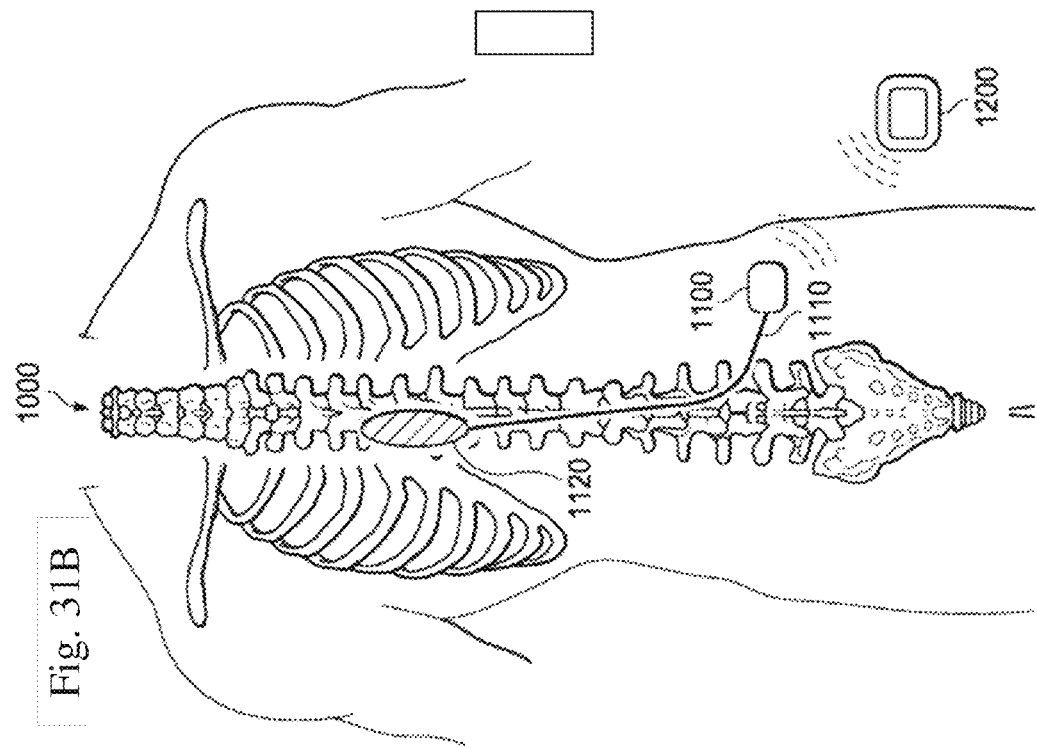
FIGS. 31A and 31B are side and posterior views of a human spine, respectively.
Figure 31B:
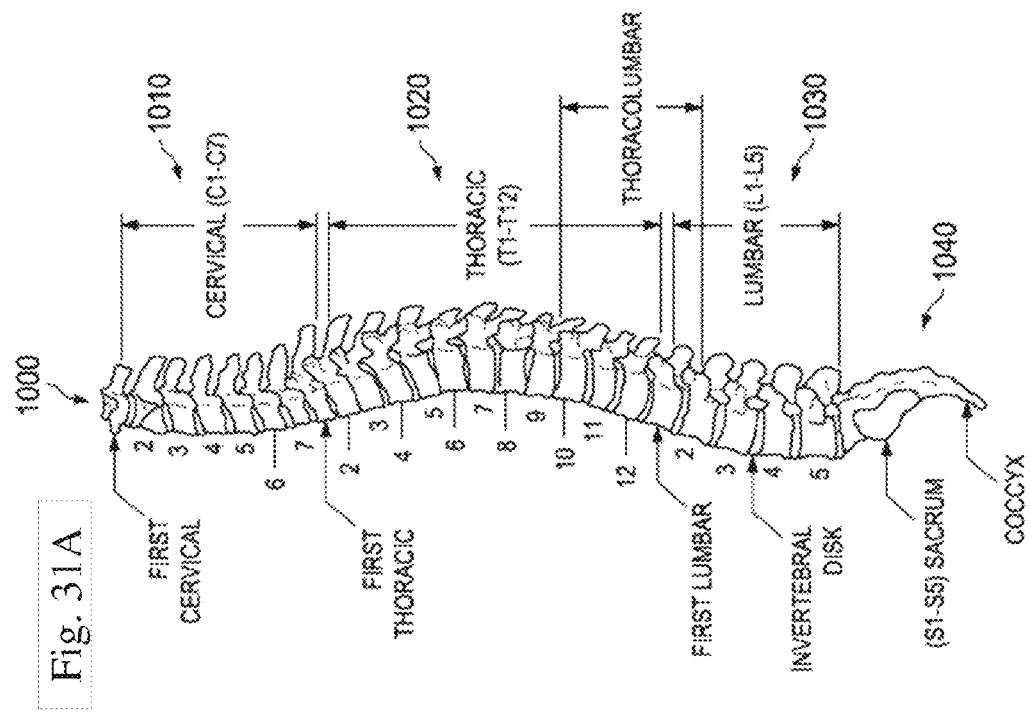

FIG. 31A is a side view of a spine 1000, and FIG. 31B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 31B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 28.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device to assist in interpreting a patient sensation map historical data set, the electronic device comprising:
   a graphical user interface configured to receive an input from a user and display a visual output to the user;
   a memory storage component configured to store programming code;
   a database storage component configured to store a plurality of the patient sensation map historical data; and
   a computer processor configured to execute the programming code to perform the following tasks:
   displaying a virtual control mechanism on the graphical user interface;
   detecting, through the graphical user interface, one engagement of the virtual control mechanism;
   displaying, in response to the one engagement of the virtual control mechanism, a visualization of a migration of a patient sensation map on the graphical user interface, the patient sensation map including a pain map and a stimulation map, wherein the visualization depicts the migration of the patient sensation map over a historical time on a virtual human body model by displaying the patient sensation map historical data in response to the one engagement;

calculating a numeric value representing an overlap coverage between the pain map and the stimulation map; and displaying the calculated numeric value in the graphical user interface;

in response to a determination that an excessive stimulation area is present, displaying a symbol next to the displayed calculated numeric value, the symbol indicating that the excessive stimulation area is present; and in response to a determination that the excessive stimulation area is no longer present, removing the symbol.

2. The electronic device of claim 1, wherein the calculating comprises calculating the numeric value by dividing a size of an overlap region between the pain map and the stimulation map by a size of the pain map.

3. The electronic device of claim 1, wherein:
the virtual control mechanism comprises a slider bar and a marker configured to be moved along the slide bar;
a length of the slider bar corresponds to a predefined period of time;
the detecting of the one engagement of the virtual control mechanism comprises detecting a movement of the marker along the slider bar; and
the displaying of the visualization of the migration of the patient sensation map comprises automatically updating the patient sensation map in response to the detected movement of the marker along the slider bar.

4. The electronic device of claim 1, wherein the tasks further comprise:
displaying only a portion of the stimulation map that does not overlap with the pain map in response to a user gesture-based input received from the graphical user interface; or
hiding an overlap region between the pain map and the stimulation map in response to a user gesture-based input received from the graphical user interface.

5. The electronic device of claim 1, wherein:
the virtual control mechanism comprises a virtual button;
the detecting of the one engagement of the virtual control mechanism comprises detecting a press of the virtual button; and
in response to the detected press of the virtual button, the visualization is automatically played as animation sequence in its entirety in an absence of further user input.

6. The electronic device of claim 1, wherein the tasks further comprise: sending the patient sensation map historical data to a remote server for a comparative analysis, wherein the sending the patient sensation map historical data comprises removing private information of the patient associated with the patient sensation map historical data.

7. The electronic device of claim 1, wherein:
the electronic device comprises a clinician programmer having the graphical user interface that includes a touchscreen; and
the detecting of the one engagement is performed via the touchscreen.

8. The electronic device of claim 1, wherein each patient sensation map is associated with a respective stimulation therapy that includes one or more stimulation programs.

9. The electronic device of claim 1, wherein the symbol comprises a "+" sign.

10. A medical system, comprising:
one or more medical devices configurable to deliver a medical therapy to a patient;
a database storage component configured to store a plurality of the patient sensation map historical data; and
an electronic device that includes:
a graphical user interface configured to receive an input from a user and display a visual output to the user;
a memory storage component configured to store computer instructions; and
a processor component configured to execute the computer instructions to perform the following tasks:
displaying a virtual control mechanism on the graphical user interface;
detecting, through the graphical user interface, one engagement of the virtual control mechanism;
displaying, in response to the one engagement of the virtual control mechanism, a visualization of a migration of a patient sensation map on the graphical user interface, the patient sensation map including a pain map and a stimulation map, wherein the visualization depicts the migration of the patient sensation map over a historical time on a virtual human body model by displaying the patient sensation map historical data in response to the one engagement;
calculating a numeric value representing an overlap coverage between the pain map and the stimulation map; and
displaying the calculated numeric value in the graphical user interface;
in response to a determination that an excessive stimulation area is present, displaying a symbol next to the displayed calculated numeric value, the symbol indicating that the excessive stimulation area is present; and
in response to a determination that the excessive stimulation area is no longer present, ceasing the displaying of the symbol.

11. The medical system of claim 10, wherein the database storage component is located in a server remotely located from the electronic device.

12. The medical system of claim 11, wherein the remote server is configured to perform a comparative analysis based on the patient sensation map historical data.

13. The medical system of claim 10, wherein the calculating comprises calculating the numeric value by dividing a size of an overlap region between the pain map and the stimulation map by a size of the pain map.

14. The medical system of claim 10, wherein:
the virtual control mechanism comprises a slider bar and a marker configured to be moved along the slide bar;
a length of the slider bar corresponds to a predefined period of time;
the detecting of the one engagement of the virtual control mechanism comprises detecting a movement of the marker along the slider bar; and
the displaying of the visualization of the migration of the patient sensation map comprises automatically updating the patient sensation map in response to the detected movement of the marker along the slider bar.

15. The medical system of claim 10, wherein the tasks further comprise:
displaying only a portion of the stimulation map that does not overlap with the pain map in response to a user gesture-based input received from the graphical user interface; or
hiding an overlap region between the pain map and the stimulation map in response to a user gesture-based input received from the graphical user interface.

16. The medical system of claim 10, wherein:
the virtual control mechanism comprises a virtual button;
the detecting of the one engagement of the virtual control mechanism comprises detecting a press of the virtual button; and
in response to the detected press of the virtual button, the visualization is automatically played as animation sequence in its entirety in an absence of further user input.

17. The medical system of claim 10, wherein:
wherein the electronic device comprises a clinician programmer having the graphical user interface that includes a touchscreen; and
the detecting of the one engagement is performed via the touchscreen.

18. The medical system of claim 10, wherein each patient sensation map is associated with a respective stimulation therapy that includes one or more stimulation programs.

19. The medical system of claim 10, wherein the symbol comprises a "+" sign.

20. A method of assisting in interpreting a patient sensation map historical data, the method comprising:
storing, in a database storage, a plurality of the patient sensation map historical data;
providing a graphical user interface configured to receive an input from a user and display a visual output to the user;
displaying a virtual control mechanism on the graphical user interface;
detecting, through the graphical user interface, one engagement of the virtual control mechanism;
displaying, in response to the one engagement of the virtual control mechanism, a visualization of a migration of a patient sensation map on the graphical user interface, the patient sensation map including a pain map and a stimulation map, wherein the visualization depicts the migration of the patient sensation map over a historical time on a virtual human body model by displaying the patient sensation map historical data in response to the one engagement;
calculating a numeric value representing an overlap coverage between the pain map and the stimulation map; and
displaying the calculated numeric value in the graphical user interface:
in response to a determination that an excessive stimulation area is present, displaying a symbol next to the displayed calculated numeric value, the symbol indicating that the excessive stimulation area is present; and
in response to a determination that the excessive stimulation area is no longer present, no longer displaying the symbol.

21. The method of claim 20, wherein the calculating comprises calculating the numeric value by dividing a size of an overlap region between the pain map and the stimulation map by a size of the pain map.

22. The method of claim 20, wherein:
the displaying of the virtual control mechanism comprises displaying a slider bar and a marker configured to be moved along the slide bar, wherein a length of the slider bar corresponds to a predefined period of time;
the detecting of the one engagement of the virtual control mechanism comprises detecting a movement of the marker along the slider bar; and
the displaying of the visualization of the migration of the patient sensation map comprises automatically updating the patient sensation map in response to the detected movement of the marker along the slider bar.

23. The method of claim 20, further comprising:
displaying only a portion of the stimulation map that does not overlap with the pain map in response to a user gesture-based input received from the graphical user interface; or
hiding an overlap region between the pain map and the stimulation map in response to a user gesture-based input received from the graphical user interface.

24. The method of claim 20, wherein:
the virtual control mechanism comprises a virtual button;
the detecting of the one engagement of the virtual control mechanism comprises detecting a press of the virtual button; and
in response to the detected press of the virtual button, the visualization is automatically played as animation sequence in its entirety in an absence of further user input.

25. The method of claim 20, wherein the providing of the graphical user interface, the displaying of the virtual control mechanism, the detecting of the one engagement of the virtual control mechanism, and the displaying of the visualization are each performed by a clinician programmer having the graphical user interface that includes a touchscreen, and wherein the detecting of the one engagement is performed via the touchscreen.

26. The method of claim 20, wherein each patient sensation map is associated with a respective stimulation therapy that includes one or more stimulation programs.

27. The method of claim 20, wherein the symbol comprises a "+" sign.

* * * * *